(12) United States Patent
Zaphiropoulos et al.

(10) Patent No.: US 6,881,833 B1
(45) Date of Patent: Apr. 19, 2005

(54) COMPONENT IN THE HEDGEHOG SIGNALLING PATHWAY

(75) Inventors: Peter G. Zaphiropoulos, Tullinge (SE);
Anne Birgitte Unden, Djursholm (SE);
Rune Toftgård, Skärholmen (SE);
Fahimeh Rahnama, Stockholm (SE);
Robert E. Hollingsworth, Research Triangle Park, NC (US)

(73) Assignees: Karolinska Innovations AB, Stockholm (SE); Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/807,007

(22) PCT Filed: Oct. 6, 1999

(86) PCT No.: PCT/SE99/01784

§ 371 (c)(1),
(2), (4) Date: Jul. 9, 2001

(87) PCT Pub. No.: WO00/20037

PCT Pub. Date: Apr. 13, 2000

(30) Foreign Application Priority Data

Oct. 6, 1998 (SE) ............................................... 9803393

(51) Int. Cl.[7] .............................................. C07H 21/04
(52) U.S. Cl. .................... 536/23.5; 435/320.1; 530/350
(58) Field of Search ............................... 536/23.5, 24.1; 435/320.1, 325, 252.1, 8; 530/300, 350

(56) References Cited

U.S. PATENT DOCUMENTS 6,309,879 B1 * 10/2001 Bumcrot 6,348,575 B1 * 2/2002 de Sauvage et al.

FOREIGN PATENT DOCUMENTS

| EP | A2-0879888 | 11/1998 |
| WO | A2-9745541 | 12/1997 |
| WO | A1-9929854 | 6/1999 |

OTHER PUBLICATIONS

Lazar et al., Molecular and Cellular Biology 8:1247–52, 1988.*
The Boehinger Mannheim Catalog, p. 557, 1991.*
Lin et al., Biochemistry 14:1559, 1975.*
Burgess et al., The Journal of Cell Biology 111:2129–2138, 1990.*
Schwartz et al., PNAS 84:6408–11, 1987.*
Motoyama et al., Nature Genetics 18:104–106, 1998.*
Carpenter et al., Journal of Clinical Investigation Online, vol. 95, No. 23, pp. 13630–13634 (1998).
Motoyama et al. Nature Genetics, vol. 18, pp. 104–106 (1998).
Takabatake et al., FEBS Letters, vol. 410, pp. 485–489 (1997).

* cited by examiner

*Primary Examiner*—Larry R. Helms
(74) *Attorney, Agent, or Firm*—Birch, Stewart, Kolasch & Birch, LLP

(57) ABSTRACT

The present invention relates to a novel human patched-like gene (PTCH2), which for the first time has been cloned and sequenced. Several alternatively spliced mRNA forms of PTCH2 have been identified, including transcripts lacking segments thought to be involved in sonic hedgehog (SHH) binding and mRNAs with differentially defined 3' terminal exons. Further, the invention also relates to the protein encoded by the present PTCH2 as well as to functional analogues and variants thereof.

6 Claims, 13 Drawing Sheets

The intron sequences between exons 2 - 3 and exons 18 - 19 are missing (introns: small letters, exons: capital letters). Small letters in the first exon indicate nucleotides that have not been unambigouisly determined.

*Exon 1*
```
   1 CGGGTGAATC CCGGCGCCGC GCCCCGGACC CGCAGCTCCC TGCACTCCTC
  51 CCTCCCAGCC GCTTTAACAC CCACACCCCA CAGTCTCTCC CACGsCCGCG
 101 CCTTGGCGGC CCCACTGAAT CCCTACGCGG GGCCCAGCGG TACCGGAGA
 151 CCGGGCTAGC CTATGGGAGC GCCCAGATAA CGCGGGTTGG GGGCGCCCGC
 201 GCCCcCATCC CCGCCAGCAT GACTCGATCG CCGCCCCTCA GAGAGCTGCC
 251 CCCGAGTTAC ACACCCCCAG CTCGAACCGC AGCACCCCAG gtgagtagag
 301 ggggagctgg aagaaggaag agagcggagc caggtctgtc actcgggcct
 351 ctgcaaggtt tgtgatgtct tgaagtgccg agtgtcatta gatgtctgaa
 401 ggcaagtgag agccagcacc gcaagcaagt tgtgcgtgtg tgtcggtgtg
 451 tctgtgccgg tgtctcctca tcgtctggcc agtgagaatg aatgtctgtg
 501 ggttcacctc tgtgtccacc cgacgacagg tgtgtgtaca tatgtatcct
 551 gctctcagaa aatgggccta tgccgccggg cgcggtgact cacgcctgta
 601 atcccaacac tgggaggctg aggcaggcag attacctgag gtcaggagtt
 651 cgagaccagc caggccaaca tggggaaact ctgtctctac taaaaataaa
 701 aattagcagg gcgtggtggc gggcgcctgt agtcccaact actcgggagg
 751 ctgaggcagg agaatctctt gaacctggga ggcggaggtt gcagtcaagc
 801 cgagatcaca ccactgcact ccagccaggg caacagagcg agatgcgtct
 851 caaaaaaaaa aaaaaaaaa aaaaggagag aaaacaaaaa gaaagaaag
 901 gaaaataggc ctatgccttc ctcaggtgtg tgctggggat ggtgggtgtt
 951 acatcttcca agtctgggcc tgtgtctgtg ttggtgctcc ctgtcccaca
1001 tccagaaatc aagaagcgag ggctgggcag cagatataca gggtgagaag
```

Fig.1A

```
1051  ggaaggattt catgcattgt tacagtgatg cctggctgac ccttctcttt
              EXON 2
1101  ccatcccagA TCCTAGCTGG GAGCCTGAAG GCTCCACTCT GGCTTCGTGC
1151  TTACTTCCAG GGCCTGCTCT TCTCTCTGGG ATGCGGGATC CAGAGACATT
1201  GTGGCAAAGT GCTCTTTCTG GGACTGTTGG CCTTTGGGGC CTGGCATTA
1251  GGTCTCCGCA TGGCCATTAT TGAGACAAAC TTGGAACAGC TCTGGGTAGA
1301  AGTGGGCAGC CGGGTGAGCC AGGAGCTGCA TTACACCAAG GAGAAGCTGG
1351  GGGAGGAGGC TGCATACACC TCTCAGATGC TGATACAGAC CGCACGCCAG
1401  GAGGGAGAGA ACATCCTCAC ACCCGAAGCA CTTGGCCTCC ACCTCCAGGC
1451  AGCCCTCACT GCCAGTAAAG TCCAAGTATC ACTCTATGGG AAG.......
1501  .......... .......... .......... .......... .........g
1551  tgagtctggc tgagcccctg agcagctggg ggcgaggcgt gctgtggggg
1601  ttctggagtg ggaatcccct tcttctgctg atctcctatg ccctggcta
              EXON 4
1651  ttgcagTCCT GGGATTTGAA CAAAATCTGC TACAAGTCAG GAGTTCCCCT
1701  TATTGAAAAT GGAATGATTG AGCGGgtaag tgtcctgaga gggagtagag
1751  gcagaacttt ttctgtagcg tgggaggact cagagaccga gcaagcccca
1801  cagcctgcaa tctgccccct taaaactaag gaggggatt gcagagggca
1851  tcctacaaag gttgtggggc aggactgacg tggcccgggg tatccctggc
              EXON 5
1901  agATGATTGA GAAGCTGTTT CCGTGCGTGA TCCTCACCCC CCTCGACTGC
1951  TTCTGGGAGG GAGCCAAACT CCAAGGGGGC TCCGCCTACC TGCCgtgagt
2001  gccactcctg gggccctgct tcatctcccg ctggggactc tccagcaga
2051  aaggagggt ctggggaatg aggatgatca aaaccttacc aaggtcctaa
2101  ttacctccca ggccaggaac agagagcatg ggcttcccca aggctctctc
2151  cacatcctcc ttctctttcc ctctcaagga aggaagacct gacttattta
2201  cacaaaacta aacacaaaga tctgtaagat ctgagcaaag gagaaaaaga
2251  tccccacaaa gaggctttgc tgggggaaat tacctaggtg tttgctaagc
2301  cattgcccag gccagaaaga aaacctgcta caggcatgtg cctgctggtt
2351  gtatattaga accaagcaca cagcttggta aggaactcag tggggccttt
```

Fig.1B 2401 ctgggccctt tctatgtatt aggtaaccct gccctgatat tcgtctcagc
2451 cccttgtact cttctacagc tcactgtagc accctggtgg gcccatgcag
2501 cctggcagtt ctgagaagct gaggcttgca caccctccat atggaaggac
2551 aaatcggcag ataagaggag ggtggggtac agcatggcgc cccagcagca
2601 gtttggagcc tgggttttcg tccctgaccc tcaccaacta taggcttttc

*EXON 6*
2651 cctcagCGGC CGCCCGGATA TCCAGTGGAC CAACCTGGAT CCAGAGCAGC
2701 TGCTGGAGGA GCTGGGTCCC TTTGCCTCCC TTGAGGGCTT CCGGGAGCTG
2751 CTAGACAAGG CACAGGTGGG CCAGGCCTAC GTGGGGCGGC CTGTCTGCA
2801 CCCTGATGAC CTCCACTGCC CACCTAGTGC CCCCAACCAT CACAGCAGGC
2851 AGgtgggttc aaccaggtc tgccagggaa aggctgtttt ccttcccttt
2901 cccttcctca tactcctgtg ttctggggga gctgactgct ctgtgccctg
2951 accccccact tcctggccat tattaccctg ctcccacagt gccaggcccc
3001 caatgttcca ttcccattca gttatcctac ggagccctca agtggtatat
3051 atgaatccct ttttcctttt ctaagcctag ataaggctgg acttcttttt
3101 ttttttttt ttgagtctca ctctgtcacc caggctggag tgcagtagtt
3151 cgatcttggc tcactgcaac ctcggctcaa gcaattctcc tgccttagcc
3201 tcctgagtag ctgggattac aggtgcccac caccatgccc ggctaatttt
3251 tattagcctc ccaaagtgct gggattacag gcgtgagcca ctgcgcctgg
3301 ccaaggctgg acttttatc aaaatagact aatacaggga aactaagaac
3351 acagcaggta agcatgaata tcatacctgg tttcccaggt ttctttgtgg
3401 ccctgcaaat gtggtacttt tttcagaatc cgccagttac accagctcct
3451 cccagaagcc tacttccagg cctctgcttc cccttggggc ttcctgtctg
3501 cgggatacta gctgttcact cctgcagagc agtcaagagg ctcagaatag
3551 ttacctacac tccagcccta ctgagcttca tggcagcgtg gttcctggag
3601 gtggaagccc agggacactc agttatccac ggccagggcc ttgagcatta

*EXON 7*
3651 acccctcctg ttcccctcca gGGCTCCCAA TGTGGCTCAC GAGCTGAGTG
3701 GGGGCTGCCA TGGCTTCTCC CACAAATTCA TGCACTGGCA GGAGGAATTG

Fig.1C

3751 CTGCTGGGAG GCATGGCCAG AGACCCCCAA GGAGAGCTGC TGAGgtaggg
3801 tctcctctgg gagttggtga ggggactctg ttcatgagaa cccatactgt
3851 aatgccaggc agctctggca aaaggccctt cacatccctc accaggtgtt
                                                                                      *EXON 8*
3901 tgggccagct ctgacccctg gttctcccac accccacca gGGCAGAGGC
3951 CCTGCAGAGC ACCTTCTTGC TGATGAGTCC CCGCCAGCTG TACGAGCATT
4001 TCCGGGGTGA CTATCAGACA CATGACATTG GCTGGAGTGA GGAGCAGGCC
4051 AGCACAGTGC TACAAGCCTG GCAGCGGCGC TTTGTGCAGg tcggtatgga
4101 caaggacaag gggggtgccc tgaggccatt ccctcctcct gccccctcct
                      *EXON 9*
4151 atccaccctg tttctccagC TGGCCCAGGA GGCCCTGCCT GAGAACGCTT
4201 CCCAGCAGAT CCATGCCTTC TCCTCCACCA CCCTGGATGA CATCCTGCAT
4251 GCGTTCTCTG AAGTCAGTGC TGCCCGTGTG GTGGGAGGCT ATCTGCTCAT
4301 Ggtgggtctt gcacctggca ccttgccccc accccacctc caaccagtgc
                                                                                    *EXON 10*
4351 ccaccctggg agccctgag actgcccttt cccccacag CTGGCCTATG
4401 CCTGTGTGAC CATGCTGCGG TGGGACTGCG CCCAGTCCCA GGGTTCCGTG
4451 GGCCTTGCCG GGTACTGCT GGTGGCCCTG GCGGTGGCCT CAGGCCTTGG
4501 GCTCTGTGCC CTGCTCGGCA TCACCTTCAA TGCTGCCACT ACCCAGgtac
4551 gccaggactg cagggcagac tcagtgccag tcaccaggct tcacgggtcc
                                                             *EXON 11*
4601 tcagctgccc gctcctctgc ccctccagGT GCTGCCCTTC TTGGCTCTGG
4651 GAATCGGCGT GGATGACGTA TTCCTGCTGG CGCATGCCTT CACAGAGGCT
4701 CTGCCTGGCA CCCCTCTCCA Ggtggggcct tgtccccag ggctcatctg
4751 aggcagctca gcttactggt taagagcctc ttggttcaag tgaccttgg
4801 gctgctaatg aacctcggtg cctcttgtcc ccatctgtaa acaggggaaa
4851 taatagtgct gtgtcctaag ggttattgtt tggatcagtg aggtaactca
4901 agttgaatgc ttagaacagc ccatcatacg tacatggtac ccaataaatg
4951 ctagccactg tgttatgact gccccacctc tgcaccccaa gttcctgagc
5001 ctccccttca ctccactttg acacggcccc tcccttgtga cctgagggca
                                                                         *EXON 12*
5051 ggtccccact ctgtcctggc agGAGCGCAT GGGCGAGTGT CTGCAGCGCA

Fig.1D

```
5101  CGGGCACCAG TGTCGTACTC ACATCCATCA ACAACATGGC CGCCTTCCTC
5151  ATGGCTGCCC TCGTTCCCAT CCCTGCGCTG CGAGCCTTCT CCCTACAGGC
5201  GGCCATAGTG GTTGGCTGCA CCTTTGTAGC CGTGATGCTT GTCTTCCCAG
5251  CCATCCTCAG CCTGGACCTA CGGCGGCGCC ACTGCCAGCG CCTTGATGTG
5301  CTCTGCTGCT CTCCAGgta ctgcgtgcgc cccagccct tcctcccgtg
5351  acccacgcca gcctgtcccc tcaccagcat ttcaaggcac agacctgtca
                                      EXON 13
5401  tccactctct acctcttcca gTCCCTGCTC TGCTCAGGTG ATTCAGATCC
5451  TGCCCCAGGA GCTGGGGGAC GGGACAGTAC CAGTGGGCAT TGCCCACCTC
5501  ACTGCCACAG TTCAAGCCTT TACCCACTGT GAAGCCAGCA GCCAGCATGT
5551  GGTCACCATC CTGCCTCCCC AAGCCCACCT GGTGCCCCCA CCTTCTGACC
5601  CACTGGGCTC TGAGCTCTTC AGCCCTGGAG GGTCCACACG GGACCTTCTA
5651  GGCCAGGAGG AGGAGACAAG GCAGAAGGCA GCCTGCAAGT CCCTGCCCTG
5701  TGCCCGCTGG AATCTTGCCC ATTTCGCCCG CTATCAGTTT GCCCCGTTGC
5751  TGCTCCAGTC ACATGCTAAG gtaagactgg gcagagcagg gcagagactt
5801  agcatctctg ggcccagaag ggcagagagg gcttagtcca ctgcctgagg
                                                                EX
5851  ggctgggggc agccctgggg tctccagctt agttgctaca tcccgcagGC
      XON 14
5901  CATCGTGCTG GTGCTCTTTG GTGCTCTTCT GGGCCTGAGC CTCTACGGAG
5951  CCACCTTGGT GCAAGACGGC CTGGCCCTGA CGGATGTGGT GCCTCGGGGC
6001  ACCAAGGAGC ATGCCTTCCT GAGCGCCCAG CTCAGGTACT CTCCCTGTA
6051  CGAGGTGGCC CTGGTGACCC AGGGTGGCTT TGACTACGCC CACTCCCAAC
6101  GCGCCCTCTT TGATCTGCAC CAGCGCTTCA GTTCCCTCAA GGCGGTGCTG
6151  CCCCCACCGG CCACCCAGGC ACCCGCACC TGGCTGCACT ATTACCGCAA
6201  CTGGCTACAG Ggtgagaggc gaggagacgg gcagggaggg gtgctgcagg
6251  gagaaacgcc ctggggccac cagctaatag aaccctatcc tggtctcccc
      EXON 15
6301  cagGAATCCA GGCTGCCTTT GACCAGGACT GGGCTTCTGG GCGCATCACC
6351  CGCCACTCGA CCGCAATGGC TCTGAGGATG GGGCCCTGGC CTACAAGCTG
6401  CTCATCCAGA CTGGAGACGC CCAGGAGCTT CTGGATTTCA GCCAGgttgg
```

Fig.1E

```
6451  gagagggctg gaggggtcca ctagtacagg ggctgcaggc ctcctgggcc
                                         EXON 16
6501  caggccttca gccctctctg cctctgcagC TGACCACAAG GAAGCTGGTG
6551  GACAGAGAGG GACTGATTCC ACCCGAGCTC TTCTACATGG GGCTGACCGT
6601  GTGGGTGAGC AGTGACCCCC TGGGTCTGGC AGCCTCACAG GCCAACTTCT
6651  ACCCCCCACC TCCTGAATGG CTGCACGACA AATACGACAC CACGGGGGAG
6701  AACTTTCGCA gtgagtcttg gggggagctc ggcaagagcc tcagcctcgc
6751  ccacacaagc cctgagcctg aggccctgcc cactctgccc cgtgctcacc
                                                          EXON 17
6801  gccctgtccc tctccctctt ctcccttccc ctcccctcca cagTCCCGCC
6851  AGCTCAGCCC TTGGAGTTTG CCCAGTTCCC TTTCCTGCTG CGTGGCCTCC
6901  AGAAGACTGC AGACTTTGTG GAGGCCATCG AGGGGGCCCC GGCAGCATGC
6951  GCAGAGGCCG GCCAGGCTGG GGTGCACGCC TACCCCAGCG GCTCCCCCTT
7001  CCTCTTCTGG GAACAGTATC TGGGCCTGCG GCGCTGCTTC CTGCTGGCCG
7051  TCTGCATCCT GCTGGTGTGC ACTTTCCTCG TCTGTGCTCT GCTGCTCCTC
7101  AACCCCTGGA CGGCTGGCCT CATAgtgagt gcttgcagga gtggggacag
7151  agacacccca cccttccctg cccagcctgt catccctcct gccaggagcc
                                         EXON 18
7201  ctctgtgagc cctgtctccc tcagGTGCTG GTCCTGGCGA TGATGACAGT
7251  GGAACTCTTT GGTATCATGG GTTTCCTGGG CATCAAGCTG AGTGCCATCC
7301  CCGTGGTGAT CCTTGTGGCC TCTGTAGGCA TTGGCGTTGA GTTCACAGTC
7351  CACGTGGCTC TGGGCTTCCT GACCACCCAG GGCAGCCGGA ACCTGCGGGC
7401  CGCCCATGCC CTTGAGCACA CATTTGCCCC CGTGACCGAT GGGGCCATCT
7451  CCACATTGCT GGGTCTGCTC ATGCTTGCTG GTTCCCACTT TGACTTCATT
7501  GTAAG..... .......... .......... .......... ..........
7551  .......... gtagggaggg ctcggggcag ggaggcaggg ctcaggacag
                                         EXON 20
7601  gcctgggctg actccccccca caccctaccc ctagGTACTT CTTTGCGGCG
7651  CTGACAGTGC TCACGCTCCT GGGCCTCCTC CATGGACTCG TGCTGCTGCC
7701  TGTGCTGCTG TCCATCCTGG GCCCGCCGCC AGAGgtgacc acaccctcgg
7751  caccatccct ctactcccag cccaagggac ggggtaggga gaggcaaggg
```

Fig.1F

```
7801  aagggacaga gccctgtggc ccacagacag gtacctcccc aacaggtgcc
7851  accagctgaa ggtggcagcc tcctcctttc cccagacacc atgttcctgc
7901  ccctcagccc tcctggcttc ttcatgggac ccaccttaga cttttaggat
7951  ccagaacaag gtgcagggtt tgccccaggc ctcaacatcc tgtcgcctgc
8001  cagctctcat atcctgctgg agaccaacaa gggccccagc ttcccaacag
8051  tcatggtaat ccccagcgag atgctaaagg ggacgggagc cccaggggcc
                                                        EXON 21
8101  cgtgggctta ctggggctgg tgtctcccca cagGTGATAC AGATGTACAA
8151  GGAAAGCCCA GAGATCCTGA GTCCACCAGC TCCACAGGGA GGCGGGCTTA
8201  Ggtgggggc atcctcctcc ctgcccaga gctttgccag agtgactacc
8251  tccatgaccg tggccatcca cccaccccc ctgcctggtg cctacatcca
8301  tccagcccct gatgagcccc cttggtcccc tgctgtcact agctctggca
8351  acctcagttc caggggacca ggtccagcca ctgggtgaaa gagcagctga
8401  agcacagaga ccatgtgtgg ggcgtgtggg gtcactggga agcactgggt
8451  ctggtgttag acgcaggatg gaccctgga gggctctgct gctgctgcat
8501  cccctctccc gacccagctg tcatgggcct ccctgatatc catacagaac
8551  agccaccgat ttgcacatcc aggcctgtgt gagcctgtat ctgtgtcact
8601  tgagagtgaa agctggcact tggggctgca gtgcagccct gtccccttc
8651  ccaccccaca ccactgcctg cccagctgac caagcctgag ggaccctcca
8701  gcaccttcc gtctggtgac tcctgggcag gctctccata tccctgccca
8751  cctcctacca catccattat ttatatgaaa atgtctattt ttgtagtata
8801  catacatgtt agctatgatg aaagttttat tttttaaaga atgaaatata
8851  ttctatgtga agctatgatg aaagttttat tttttaaaga atgaaatata
8901  ttctatgtga actaatctcg aaagttttat tttttaaaga atgaaatata
8951  ttctatgtgt gcaagtgaac attagcttca gttgcttttt tttggacaga
9001  gtggggagtt tgcaagtgaa cattagctat tggaaggagc ttctctggtg
9051  ccaggacctg aggtattagc ttctctagtt ctgggtggaa aagacccag
9101  attctggatt tttgtcatat acttggtaac atcatctgga ttaagtgctt
```

Fig.1G

```
 9151  actatacaaa acgataacaa attttgttgg tgtgaaatcc tactgggttc
 9201  aatctggaga ccgagagcag aaaaaaaga accccactgt gtggctttca
 9251  gagccaccat attccagcct gcccgtctct ccagactcac ctccacctac
 9301  ctgcttcacc cgcacgggaa acggcaaggc agaggggcaa agccatgcag
 9351  caggtggaag gcgaggtgga ggcagatcag gaaagcagcc agttgaagca
 9401  gagagaggtc aacagggtct ggggagcttc tcaggaggtt tgtggaccca
 9451  gggaaaggag ccaggttcca gagcaacctc caaggcaaag gcctctgtaa
 9501  gttggttgtc ctgacagccg agaggtgtct ttggccagtc agccagtgga
 9551  tcagttgcgg gaactgctca gaaactgagg tgctagcagt tagtgaggac
 9601  acagcgtaag ttgtttgttc tgtgaaagtt gaacagctcc actaagcaga
 9651  ggccttgaag agtggccaca gccctggaat agagcacaga gcctcaccta
 9701  gaggcgtggg gaggtttgca actgcccctt cccagccata gcttaggacc
 9751  catagtctag ttcacataga ccctgggctc caaccaccca ctcaccagga
 9801  atgatcccac cccaggaaca atgcgttctc acatcccacc ccacctggac
 9851  aaaggccagg aaatcatgtt ctgaccaaaa gatacaacaa caaaaacaac
 9901  aacaacaaaa aacgcctatt gcaattgaat ccacgctaaa atgcctaaaa
 9951  agctcaagag aagcgggtag ttggcagaga acctagagta gggggtgcaa
10001  ccagcaggcc caagggaggg aggctgcatt tgggtccagc agtgtttggg
10051  tcaccaagaa gggccttcta ggtggagcag agagagctca ccaggccaga
10101  atagtgcaaa gggggtcagc cctcagtgcc acttaccagc ggagtaaccc
                                                                   E
10151  tgggcaagtt agccagcctc actaagcctc cccatcttca tctttccagG
       XON 22
10201  CCCGAGGAGA TCTAGCCTCT GCCTCCCACC CCAGCACCCC CTCATCAGAC
10251  ACAAGGAGCG CCACTGTCTG GACAGGCTGA ATTGGTCTTC GGGTCCCTAA
10301  TTTCTCATAC GCCATTCCCT CTGCCTAGAA CACTTTCTCA CCTCCCCTTG
10351  ATGTGACCCC ATATCACCCT TCGAGGTGAA TTGGATCGGA TGCCATCTCC
10401  TCCAGGAGGG GTGGGTCGT GCCTCCTGTG AGGTCCCAGT GCCCCTGAGT
10451  GTCTGTGCCC GTCTGTTTCC CCGTCCCTCT CTCTAAGCCC GGAGGCTTAC
```

Fig.1H

```
10501  TGCGGGTAAG GACGGCGGGA CAGGACCTTA ACCCCTGGGA CGAACACCAG
10551  CTCCGCAAAG GACTCCGCAC CCGGCGCCGC CCACGGGGTG CGGGTCCCAG
10601  GAGGACCAGC AGAGAGGAGC ATAGGAGAGC AAAGGAGATC AGTGACCCAT
10651  GGCTTCCCCG GTGGCGCGGA ACAGCCCGGA GCCGCCTGTG ATTTGCATAC
10701  CCATGGTGCA CCACGAAAAG ATACCCTCAA GATGCTTGCA CTCCCTCTGT
10751  GCGCGCATTT CTGCACTGTT TTAGAGCATG ATGCCTCTTA CACGCATCTG
10801  TGTGCATAAA CTACATATAG GGAGTGCGTA CCACGCAGGC ATCCAACAAC
10851  CATAAGTGTG TTAAGTGTTA GTTCTCCCTG CGAGGTTCGA AGCGGAAGTC
10901  ACGAATATAC TCGGGTTTCT CTTCAAAGCG CATAAATCTT TCGCCTTTTA
10951  CTAAAGATTT CCGTGGAGAG AAAGTTGTGA GTTTTTATTC AATTTTTTGA
11001  GGCCTCTTAT TTCCTGAGGC TACATTTTTA AGTATTAAAA GTTAGGCAAC
11051  TACAAAAAAA AAAAAAAA
```

Fig.1I

```
  1 ........................MTRSPPLRELP....... 11
                            . |...|| :
  1 MASAGNAAEPQDRGGGGSGCIGAPGRPAGGGRRRRTGGLRRAAAPDRDYL 50

12 ..PSYTPPARTAAPQI...LAGSLKAPLWLRAYFQGLLFSLGCGIQRHCG 56
    |||..:|   | .||    |.: ||||||||| || |||.||| ||::||
 51 HRPSYCDAA.FALEQISKGKATGRKAPLWLRAKFQRLLFKLGCYIQKNCG 99

57 KVLFLGLLAFGALALGLRMAIIETNLEQLWVEVGSRVSQELHYTKEKLGE 106
    |.|..||| |||:|:||: | :|||:|:|||||:|||.||:||::|:||
100 KFLVVGLLIFGAFAVGLKAANLETNVEELWVEVGGRVSRELNYTRQKIGE 149

107 EAAYTSQMLIQTARQEGENILTPEALGLHLQAALTASKVQVSLYGKSWDL 156
    || :..|::|||:::||.|:||.|||   ||:.|| ||:|:| :|.: |.|
150 EAMFNPQLMIQTPKEEGANVLTTEALLQHLDSALQASRVHVYMYNRQWKL 199

157 NKICYKSGVPLIENGMIERMIEKLFPCVILTPLDCFWEGAKLQGGSAYLP 206
    :..|||||   :.|.| ::..:|| |:||:|:||||||||||||:|.|||
200 EHLCYKSGELITETGYMDQIIEYLYPCLIITPLDCFWEGAKLQSGTAYLL 249

207 GRPDIQWTNLDPEQLLEELGPFA.SLEGFRELLDKAQVGQAYVGRPCLHP 255
    |:|.:.|||:|| ::||||  .:.   :::: |:|:||:||::|:||||:|
250 GKPPLRWTNFDPLEFLEELKKINYQVDSWEEMLNKAEVGHGYMDRPCLNP 299

256 DDLHCPPSAPNHHSRQAPNVAHELSGGCHGFSHKFMHWQEELLLGGMARD 305
    .| .||:.|||.:| .: ::|  |.|||||:|:|:|||||||||::|| .::
300 ADPDCPATAPNKNSTKPLDMALVLNGGCHGLSRKYMHWQEELIVGGTVKN 349

306 PQGELLRAEALQSTFLLMSPRQLYEHFRGDYQTHDIGWSEEQASTVLQAW 355
    . |.|:.|.|||.  | ||.|:|:|||||:|    .|.|.|:.|...:|:||
350 STGKLVSAHALQTMFQLMTPKQMYEHFKGYEYVSHINWNEDKAAAILEAW 399

356 QRRFVQLAQEALPENASQQIHAFSSTTLDDILHAFSEVSAARVVGGYLLM 405
    || :|:::.::.:::|..|..: .|..||||||||..||:||. ||.:|||||
400 QRTYVEVVHQSVAQNSTQKVLSFTTTTLDDILKSFSDVSVIRVASGYLLM 449

406 LAYACVTMLRWDCAQSQGSVGLAGVLLVALAVASGLGLCALLGITFNAAT 455
    |||||:|||||||..|||.||||||||||||.||.|||||.|:||.|||||
450 LAYACLTMLRWDCSKSQGAVGLAGVLLVALSVAAGLGLCSLIGISFNAAT 499

456 TQVLPFLALGIGVDDVFLLAHAFTEALPG..TPLQERMGECLQRTGTSVV 503
    ||||||||||:|||||||||||.| ..  .|::::| ||||.|||.||.
500 TQVLPFLALGVGVDDVFLLAHAFSETGQNKRIPFEDRTGECLKRTGASVA 549

504 LTSINNMAAFLMAALVPIPALRAFSLQAAIVVGCTFVAVMLVFPAILSLD 553
    ||||.|:.||:||||:||||||||||||||:|.|.| |:|:||||||||:|
550 LTSISNVTAFFMAALIPIPALRAFSLQAAVVVVFNFAMVLLIFPAILSMD 599

554 LRRHCQRLDVLCCFSSPCSAQVIQILPQELGDGT...........VPVG 592
    | ||. .|||::|||.||| ..|||: ||...|.             : 
600 LYRREDRRLDIFCCFTSPCVSRVIQVEPQAYTDTHDNTRYSPPPPYSSHS 649

593 IAH.....LTATVQAFTHCEASSQHVVTILPPQAHL....VPPPSDPLGS 633
    :||      : .||| |.:::: .:  |. .|...:   |... |.|::
650 FAHETQITMQSTVQLRTEYDPHTHVYYTTAEPRSEISVQPVTVTQDTLSC 699
```

COMPONENT IN THE HEDGEHOG SIGNALLING PATHWAY

This application is the national phase under 35 U.S.C. § 371 of PCT International Application No. PCT/SE99/01784 which has an International filing date of Oct. 6, 1999, which designated the United States of America.

TECHNICAL FIELD

The present invention relates to novel molecules such as proteins, polypeptides and nucleotides, involved in the hedgehog signalling pathway with putative involvement in embryonic development and carcinogenesis. The invention also relates to various novel advantageous uses of the molecules according to the invention, e.g. in diagnosis and therapy.

BACKGROUND

In the study of the development of cells, fit flies have extensively been used as a model, as they are less complex than mammalian cells.

Pattern formation takes place through a series of logical steps, reiterated many times during the development of an organism. Viewed from a broader evolutionary perspective, across species, the same sort of reiterative pattern formations are seen. The central dogma of pattern formation has been described (Lawrence and Struhl, 1996). Three interlocking and overlapping steps are defined. Firstly, positional information in the form of morphogen gradients allocate cells into non-overlapping sets, each set founding a compartment. Secondly, each of these compartments acquire a genetic address, as a result of the function of active "selector" genes, that s cell fate within a compartment and also instruct cells and their descendents how to communicate with cells in neighboring compartments. The third step involves interactions between cells in adjacent compartments, initiating new morphogen gradients, which directly organize the pattern.

Taking these steps in greater detail, one finds the first step in patterning to be the definition of sets of cells in each primordium. Cells are allocated according to their positions with respect to both dorsoventral and anterior/posterior axes by morphogen gradients. Allocation of cells in the dorsoventral axis constitutes the germ layers, such as mesoderm or neurectoderm.

In segmentation, the second step (the specification of cell fate in each compartment) is carried out by the gene engrailed and elements of the bithorax complex. Engrailed defines anterior and posterior compartments both in segmentation and in limb specification.

The third step in pattern formation, secretion of morphogens, functions to differentiate patterns within compartments (and thereby establish segment polarity). Initially, all cells within a compartment are equipotent, but they become diversified to form pattern. Pattern formation depends on gradients of morphogens, gradients initiated along compartment boundaries. Such gradients are established by a short-range signal induced in all the cells of the compartment in which the above mentioned selector gene engrailed is active. For segment polarity, this signal is Hedgehog. In the adjacent compartment the selector gene is inactive, ensuring that the cells are sensitive to the signal. The Hedgehog signal range is probably only a few rows of cells wide; responding cells become a linear source of a long-range morphogen, that diffuses outward in all directions. There are three known Hedgehogs, Sonic (SHH), Indian (IHH) and Desert (DHH). The proteins they encode can substitute each for each other, but in wildtype animals, their distinct distributions result in unique activities. SHH controls the polarity of limb growth, directs the development of neurons in the ventral neural tube and patterns somities. IHH controls endochondral bone development and DHH is necessary for spermiogenesis. Vertebrate hedgehog genes are expressed in many other tissues, including the peripheral nervous system, brain, lung, liver, kidney, tooth primordia, genitalia and hindgut and foregut endoderm.

Thus, segment polarity genes have been identified in flies as mutations, which change the pattern of structures of the body segments. Mutations in these genes cause animals to develop the changed patterns on the surfaces of body segments, the changes affecting the pattern along the head to tail axis. For example, mutations in the gene patched cause each body segment to develop without the normal structures in the center of each segment. Instead there is a mirror image of the pattern normally found in the anterior segment. Thus, cells in the center of the segment make the wrong structures, and point them in the wrong direction with reference to the over all head-to-tail polarity of the animal.

About sixteen genes in the class are known. The encoded proteins include kinases, transcription factors, a cell junction protein, two secreted proteins called wingless (WG) and the above mentioned Hedgehog (HH), a single transmembrane protein called patched (PTC) and some novel proteins not related to any known protein. All of these proteins are beleived to work together in signaling pathways that inform cells about their neighbors in order to set cell fates and polarities.

PTC has been proposed as a receptor for HH protein based on genetic experiments in flies. A model for the relationship is that PTC acts through a largely unknown pathway to inactivate both its own transcription and the transcription of the wingless segment polarity gene. This model proposes that HH protein, secreted from adjacent cells, binds to the PTC receptor, inactivates it and thereby prevents PTC from turning off its own transcription or that of wingless. A number of experiments have shown coordinate events between PTC and HH.

Human patched gene (PTCH) was recently identified as the gene responsible for the nevoid basal cell carcinoma syndrome (NBCCS), also known as the Gorlin Syndrome, which is an autosomal dominant disorder that predisposes to both cancer and developmental defects (Gorlin (1995) *Dermatologic Clinics* 13:113–125) characterized by multiple basal cell carcinomas (BCCs), medulloblastomas and ovarian fibromas as well as numerous developmental anomalities (Hahn, H., Wicking, C., Zaphiropoulos, P. G., Gailani, M. R., Shanley, S., Chidambaram, A., Vorechovsky, I., Holmberg, E., Undén, A. B., Gillies, S., Negus, K., Smyth, I., Pressman, C., Leffell, D. J., Gerrard, B., Goldstein, A. M., Dean, M., Toftgård, R., Chenevix-Trench, G., Wainright, B. and Bale, A. E. (1996): "Mutations of the human homolog of Drosophila patched in the nevoid basal cell carcinoma syndrome", Cell 85, 841–851; and Johnson, R. L., Rothman, A. L., Xie, J., Goodrich, L. V., Bare, J. W., Bonifas, J. M., Quinn, A: G., Myers, R. M., Cox, D. R., Epstein, E. H. Jr and Scott, M. P. (1996): "Human homolog of patched, a candidate gene for the basal cell nevus syndrome", Science 272, 1668–1671). PTCH codes for a membrane receptor of the autolytically cleaved (protein spliced), amino terminal domain of sonic hedgehog (SHH) (Mariago, V., Davey, R. A., Zuo, Y., Cunningham, J. M. and Tabin, C. J. (1996): "Biochemical evidence that patched is the Hedgehog receptor", Nature 384, 176–179; and Stone, D. M., Hynes, M., Armanini, M., Swanson, T. A., Gu, Q., Johnson, R. L., Scott, M. P., Pennica, D., Goddard, A., Phillips, H., Noll, M., Hooper, J. E., de Sauvage, F. and Rosenthal, A. (1996): "The tumor-suppressor gene patched encodes a candidate receptor for Sonic hedgehog", Nature 384, 129–134). In the non-signalling state, PTCH is thought to inhibit the consecutive signalling of another membrane protein, smoothened (SMO), however binding of SHH to PTCH releives this inhibition (Goodrich, L. V., Milenkovic, L., Higgins, K. M. and Scott, M. P. (1997): "Altered neural cell fates and medullablastom in mouse patched mutants", Science 277, 1109–1113). This cascade of signalling events, best characterized in Drsophila, also involves a number of intracellular components including fused (a serine threonine kinase), suppressor of fused, costal 2, and cubitus interruptus (Ruiz i Altaba, A.,: "Catching a Gli-mpse of Hedgehog" (1997) Cell 90, 193–196). The latter is a transcription factor that positively regulates the expression of target genes which also include PTCH itself.

Mutations in the PTCH gene have been identified in both sporadic and familial BCCs (Gailani, M. R., Stähle-Bäckdahl M., Leffell, D. J., Glynn, M., Zaphiropoulos, P. G., Pressman, C., Undén, A. B., Dean, M., Brash, D. E., Bale, A. E. and Toftgård, R. (1996): "The role of human homologue of Drosophila patched in sporadic basal cell carcinomas" Nature Gene 14, 78–81). The lack of the normal PTCH protein in these cells allows the constitutive signalling of SMO to occur, resulting in the accumulation of mutant PTCH mRNAs (Undén, B. A., Zaphiropolous, P. G., Bruce, K., Toftgård, R., and Stähle-Bäckdahl M. (1997): "Human patched (PTCH) mRNA is overexpressed consistently in tumor cells of both familial and sporadic basal cell carcinoma", Cancer Res. 57, 2336–2340). WO 96/11260 discloses the isolation of patched genes and the use of the PTC protein to identify ligands, other than the established ligand Hedgehog, that bind thereto.

However, there is still a need of a further understanding of the SHH/PTCH cell signalling, which may be provided by disclosure of further genes, peptides and proteins involved therein.

SUMMARY OF THE INVENTIONS

The present invention provides a significant step forward regarding the understanding of the above described pathway. By a combination of cDNA library and RACE analysis a novel human patched-like gene (PTCH2) has been cloned and sequenced. Several alternatively spliced mRNA forms of PTCH2 have been ideintified, including transcipts lacking segments thought to be involved in sonic hedgehog (SHH) binding and mRNAs with differentially defined 3' terminal exons. Accordingly, the invention relates to isolated such mRNAs as well as to cDNAs complementary thereto.

BRIEF DESCRIPTION OF THE DRAWINGS

FIG. 1 shows the genomic sequence of SEQ ID NO:5, wherein exons and introns are designated in the genomic sequence of the novel human patched 2 gene.

FIG. 2A discloses an amino acid sequence comparison of the human PTCH2 (residues 1–633 of SEQ ID NO:1)(upper lines) and PTCH1(residues 1–699 of SEQ ID NO:6) (lower lines) sequences.

DEFINITIONS

Figure 2B:
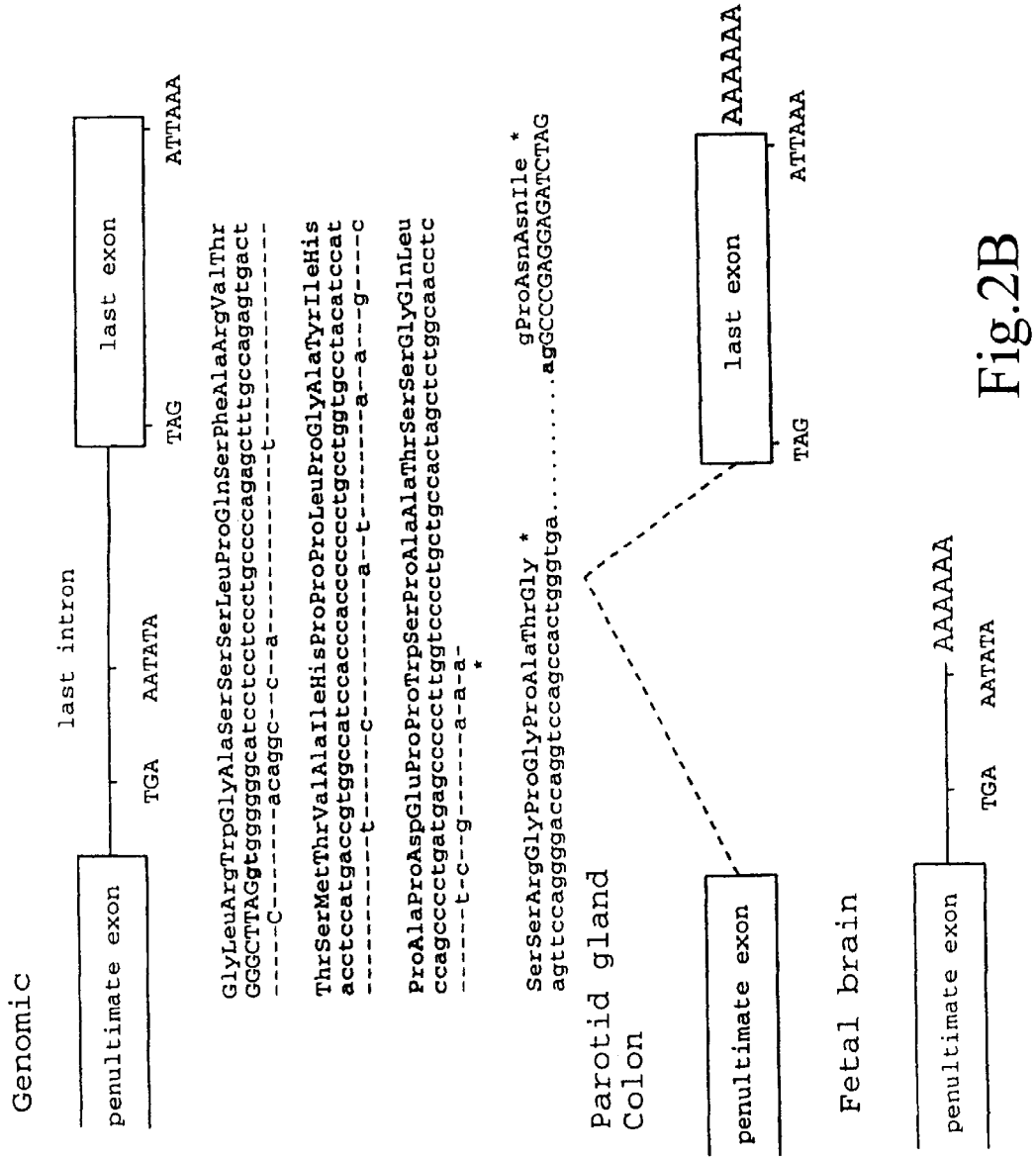
FIG. 2B is a representation of the alternative splicing events (SEQ ID NOS:7, 8, 9, 10, 11, 12, 13, 14, 15 and 16) that result in different C-termini.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The terms "isolated" "purified" or "biologically pure" refer to material which is substantially or essentially free from components which normally accompany it as found in its native state.

The term "nucleic acid" refers to a deoxyribonucleotide or ribonucleotide polymer in either single- or double-stranded form, and unless otherwise limited, encompasses known analogs of natural nucleotides that can function in a similar manner as naturally occurring nucleotides.

A "label" is a composition detectable by spectroscopic, photochemical, biochemical, immunochemical or chemical means. For example, useful labels include $^{32}$P, fluorescent dyes, electron-dense reagents, enzymes (e.g., as sommonly used in a ELISA), biotin, dioxigenin, or haptens and proteins for which antisera or monoclonal antibodies are available (e.g., the peptide of SEQ ID NO:1 can be made detectable, e.g., by incorporating a radio-label into the peptide, and used to detect antibodies specifically reactive with the peptide).

As used herein a "nucleic acid probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, C, or T) or modified bases (7-deazaguanosine, inosine, etc.) In addition, the bases in a probe may be joined by a linkage other than a phosphodiester bond, so long as it does not interfere with hybridisation. Thus, for example, probes may be peptide nucleic acids in which the constituent bases are joined by peptide bonds rather that phosphodiester linkages. It will be understood by one of skill in the art that probes may bind target sequences lacking complete complementarity with the probe sequence depending upon the stringency of the hybridisation conditions. The, probes are preferably directly labeled as with isotopes, chromophores, lumiphore, chromogens, or indirectly labeled such as with biotin to which a streptavidin complex may later bind. By assaying for the presence or absence of the probe, one can detect the presence or absence of the selct sequence or subsequence.

A "labeled nucleic acid probe" is a nucleic acid probe that is bound, either covalently, through a linker, or through ionic, van der Waals or hydrogen bonds to a label such that the presence of the probe may be detected by detecting the presence of the label bound to the probe.

The term "target nucleic acid" refers to a nucleic acid (often derived from a biological sample), to which a nucelic acid probe is designed to specifically hybridise. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid may refer to the specific subsequence of a larger nucleic acid to which the probe is directed or to the ovarall sequence (e.g., gene or mRNA) whose expression level it is desired to detect. The difference in usage will be apparent from context.

The term "recombinant" when used with reference to a cell, or nucleic acid, or vector, indices that the cell, or nucleic acid, or vector, has been modified by the introduction of a heterologous nucleic acid or the alteration of a native nucleic acid, or that the cell is derived from a cell so modified.

The term "identical" in the context of two nucleic acids or polypeptide sequences refers to the residues in the two sequences which are the same when aligned for maximum correspondence. Optimal alignment of sequences for comparison can be conducted, e.g., by the local homology algorith of Smith and Waterman (1981) *Adv. Appl. Math.* 2: 482, by the homology alignment algorithm of Needleman and Wunsch (1970) *J. Mol. Biol.* 48:443, by the search for similarity method of Pearson and Lipman (1988) *Proc. Natl. Acad. Sci. USA* 85: 2444, by computerized implementations of these algorithms (GAP, GESTFIT, FASTA, and TFASTA in the Wisconsin Genetics Software Package, Genetics Computer Group, 575 Science Dr., Madison, Wis.) or by inspection. The BLAST algorithm performs a statistical analysis of the similarity between two sequences; see e.g., Karlin and Altschul (1993) *Proc. Nat'l Acad. Sci. USA* 90: 5873–5787.

The term "substantial identity" or "substantial similarity" in the context of a polypeptide indicates that a polypeptides comprises a sequence with at least 70% sequence identity to a reference sequence, or preferably 80%, or more preferably 85% sequence identity to the reference sequence, or most preferably 90% identity over a comparison window of about 10–20 amino acid residues. An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution.

An indication that two nucleic acid sequences are substantially identical is that the polypeptide which the first nucleic acid encodes is immunologically cross reactive with the polypeptide encoded by the second nucleic acid. Another indication that two nucleic acid sequences are substantially identical is that the two molecules hybridise to each other under stringent conditions.

The phrase "hybridising specifically to", refers to the binding, duplexing, or hybridising of a molecule only to a particular nucleotide sequence under stringent conditions when that sequence is present in a complex mixture (e.g., total cellular) DNA or RNA. The term "stringent conditions" refers to conditions under which a probe will hybridise to its target subsequence, but to no other sequences. Stringent conditions are sequence-dependent and will be different in different circumstances. Longer sequences hybridise specifically at higher temperatures. Generally, stringent conditions are selected to be about 5° C. lower than the thermal melting point™ for the specific sequence at a defined ionic strength and pH. The Tm is the temperature (under defined ionic strength, pH, and nucleic acid concentration) at which 50% of the probes complementary to the target sequence hybridise to the target sequence at equilibrium. (As the target sequences are generally present in excess, at Tm, 50% of the probes are occupies at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for whort probes (e.g., 10 to 50 nucleotides) and at least about 60° C. for long probes (e.g., greater than 50 nucleotides). Stringent conditions may also be achieved with the addition of destabilizing agents such as formamide.

The term "antibody" refers to a polypeptide substantially encoded by an immunoglobulin gene or immunoglobulin genes, or fragments thereof which specifically bind and recognize an analyte (antigen).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that utilizes an antibody to specifically bind an analyte. The immunoassay is characterized by the use of specific binding properties of a particular antibody to isolate, target, and/or quantify the analyte.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antoibodies specifically immunoreactive with a protein. See harlow and Lane (1988) *Antibodies, A Laboratory Manual*, Cold Spring Harbour Publications, New York, for a description of immunoassay formats and conditions that can be used to determine specific immunoreactivity.

A "gene product", as used herein, refers to a nucleic acid whose presence, absence, quantity, or nucleic acid sequence is indicative of a presence, absence, quantity, or nucleic acid composition of the gene. Gene products thus include, but are not limited to, and mRNA transcript a cDNA reverse transcribed from an mRNA, and RNA transcribed from that cDNA, a DNA amplified from the cDNA, an RNA transcribed from the amplified DNA or subsequences of any of these nucleic acids. Polypeptides expressed by the gene or subsequences thereof are also gene products. The particular type of gene product will be evident from the context of the usage of the term.

A "modified drug" means a compound, which retains the pharmaceutical properties of the original drug or active substance while the structure thereof has been modified. Further, encompassed by the term "drug" are also compounds useful in diagnostic methods by their specific binding properties.

DETAILED DESCRIPTION OF THE INVENTION

In a first aspect, the present invention relates to an isolated human protein, or an analogue or a variant thereof, capable of participating in the human PTCH/SHH pathway during embryonic development and/or carcinogenesis, such as basal cell carcinoma. The novel protein according to the invention is encoded by a novel gene, which isolated nucleic acid is described in detail below and which is denoted patched 2 (PTCH2) due to its similarities with patched 1 (PTCH1). Accordingly, the protein according to the invention exhibits substantial differences in sequence and functions when compared to human PTCH1 protein. The protein according to the invention is best characterized by its functions which when compared to human PTCH1 are similar but distinct therefrom in certain ways, more specifically disclosed below in the section "Results and discussion". The novel human PTCH2 protein according to the invention is also distinct from the previously isolated mouse PTCH2. Thus, in the preferred embodiment thereof it comprises a substantial part of the amino acid sequence disclosed in SEQ ID NO: 1 and submitted to the GenBank under protein id no AAD17260.1. even though it is to be understood that the present invention encompasses any fragment, analogue or variant thereof exhibiting the biological functions of the PTCH2 protein disclosed herein. Thus, preferably, the present protein comprises at least about 1000, more preferably at least about 1040 and most preferably essentially all of the amino acids of the sequence denoted SEQ ID NO: 1, such as about 1100.

The proteins according to the invention are easily prepared by someone skilled in this field by recombinant DNA techniques using the molecules disclosed below or any synthetic method (see e.g. Barany and Merrifield, Solid-Phase Peptide synthesis, pp. 3–284 in The Peptides: Analysis, Synthesis, Biology, Vol. 2: Special Methods in Peptide synthesis, Part A, Merrifield et al., J. Am. Chem. Soc., 2149–2156).

The present invention also relates to the use of the peptides, polypeptides and proteins disclosed herein as lead compounds in methods aimed at finding novel substances, i.e. modified drugs, such as substances exhibiting equivalent or even more advantageous properties than the lead compounds as such. Such modified drugs may also be designed by methods of combinatorial chemistry, wherein a structurally similar compound is specifically designed e.g. by aid of computers. Alternatively, the present modified drug is identified by screening of a library of candidate compounds, e.g. using an antibody according to the invention. In the present context it is to be understood that when such a modified drug has been identified, it is possible to produce it by any other suitable technique. The invention also relates to proteomic methods wherein the present molecules are used as well as to such a use per se.

A second aspect of the present invention is a nucleic acid encoding a protein, an analogue or a variant thereof as defined above, that is, the protein coding region of the novel human isolated PTCH2 gene. The PTCH2 gene is 57% identical to PTCH1 and 91% identical to the published mouse Ptch2 sequence (see Motoyama et al., (1998), supra). Thus, preferably, the nucleic acid according to the present invention comprises at least about 3000 bases, more preferably at least about 3094 bases and most preferably essentially all of the sequence denoted SEQ ID NO: 2.

In a specific aspect, the present invention relates to the isolated human genomic PTCH2 nucleic acid comprising parts or all of the genomic sequence denoted SEQ ID NO: 5. In the disclosure of the genomic sequence shown in FIG. 1, the exon/intron structure of the present gene is shown. Further to the exons shown therein, exon 12a and 12b has also been identified, as specifically defined by SEQ ID NO:3 and SEQ ID NO:4, respectively. Interestingly, there is a splice variant that joins exon 12a to a 3' segment of exon 12b with conservation of the intronic GT-AG dinucleotides. Exons 12a and 12b are not variants, but the actual exons of the gene identified by sequencing the corresponding genomic region. (Materials and methods were as discribed beloow). Accordingly, these findings show that PTCH2 has the same intron/exon structure organization as PTCH1. In another embodiment of this aspect, the present invention relates to a transcript that has skipped only one of the exons 9 and 10 defined in FIG. 1. In an alternative embodiment, the transcript according to the invention has skipped both of exon 9 and 10. The splice variants of the present gene are discussed in more detail below in the section "Results", all of which are included within the scope of the present invention. This aspect of the invention advantageously enables design of suitable PCR primers, which in turn enables screening for mutations of all of the coding sections thereof, e.g. by SSCP analysis, sequencing, or any other suitable method known to someone skilled in this field. Thus, the novel human PTCH2 gene according to the invention has been localized by radiation hybrid mapping to chromosome 1p32–35 with D1S211 and WI-1404 as closest flanking markers and with an estimated localization 5.5cR from D1S443. This region is often lost by LOH in various different tumor types, such as neuroblastoma, melanoma, breast cancer, colon cancer etc. Accordingly, PTCH2 is a candidate for a tumor suppressor gene in this region and the present invention also encompass diagnostic methods based on this new disclosure.

To this chromosomal region, three cancer predisposition syndromes have also been mapped, namely, familial melanoma CMM1, modifier locus for familial adenomatous polyposis hMom1 and Michelin Tire Baby Syndrome. PTCH2 is further a candidate for the gene behind these heritary syndromes. The present molecules are therefore advantageously used in the context of these conditions, e.g. in therapy and/or diagnosis, such as in assays.

Further, the invention also relates to various PCR primers based on intronic sequences, allowing amplification of all coding sequence. Such primers are advantageously used for mutation screening.

Further, the present invention also relates to the any isolated nucleic acid capable of specifically hybridising to a nucleic acid according to the invention. In addition, the invention also relates to such an isolated nucleic acid which comprises one o more mutations compared to the genomic sequence as well as the use of the novel isolated nucleic acids, e.g. to identify mutations for diagnostic and/or therapeutic purposes.

Further embodiments of this aspect of the invention includes nucleic acid probes, e.g. DNA probes, labelled nucleic acids, cDNAs, RNAs etc., that is, all gene products obtainable by someone skilled in this field based on the novel isolated human PTCH2 gene.

Another aspect of the invention is a nucleic acid corresponding to any one of the splicing variants disclosed in FIG. 2B, a protein or polypeptide encoded thereof as well as various uses thereof.

As regards the preparation of nucleic acids according to the invention, any suitable recombinant DNA technique or synthetic method may be used. (For general laboratory procedures useful in this context, see e.g. Sambrook et al., Molecular Cloning, A Laboratory Manual, $2^{nd}$ ed., Vol. 1–3, Cold Spring Harbor Laboratory, Cold Spring Harbor, N.Y., 1989; Berger and Kimmel, Guide to Molecular Cloning Techniques, Methods in Enzymology, Vol. 153, Academic Press, Inc., San Diego, Calif.; Current Protocols in Molecular Biology, F. M. Ausbel et al., eds., Current Protocols (1994)).

A further aspect of the present invention is a vector comprising a nucleic acid as defined above. Vectors are e.g. useful for transforming cells in vitro or in vivo to express the proteins and peptides according to the invention and may e.g be plasmids, viruses etc.

Another aspect of the invention is a recombinant cell such as a eucaryotic, e.g. a mammalian cell, or a procaxyotic cell, e.g. a bacteria, comprising a vector as defined above. Such cells may e.g. be used to monitor expression levels of the proteins and polypeptides according to the invention in a wide variety of contexts. For example, when the effects of a drug is to be determined, the drug will be administered to the transformed organism, tissue or cell. Accordingly, model systems including such cells are another aspect of the invention.

A further aspect of the invention is an antibody, such as a monoclonal or polyclonal antibody, which specifically binds to a protein or polypeptide according to the invention. An exemplary imunuoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable haeavy chain ($V_H$) refer to these light and heavy chains, respectively.

The invention also encompasses chimeric or other antibodies that binds the present proteins or polypeptides. Further, the invention also relates to the use of the present antibodies in assays. (In this context, see e.g. *Fundamental Immunology*, Third Edition, W. E. Paul, ed., Raven Press, N.Y. 1993).

Further, the invention also relates to a recombinant cell expressing an antibody according to the invention.

In general, prokaryotes can be used for cloning the DNA sequences encoding a human anti-PTCH2 immunoglobulin chain. *E. coli* is one prokaryotic host particularly useful for cloning the DNA sequences of the present invention. Microbes, such as yeast are also useful for expression Saccharomyces is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase 2, isocytochrome C, and enzymes responsible for maltose and galactose utlization.

Mammalian cells are a particularly preferred host for expressing nucleotide segments encoding immunoglobulins or fragments thereof (see, e.g. Winnacker, *From Genes to Clones*, VCH Publishers, N.Y., 1987). A number of suitable host cell lines cable of secreting intact heterologous proteins have been developed in the art and include CHO cell lines, various COS cell lines, HeLa cells, L cells and myeloma cell lines. Preferably, the cells arm nonhuman. Expression vectors for these cells can include expression control sequences, such as an origin of replication, a promoter, an enhancer (Queen et al. (1986) *Immunol. Rev.* 89:49), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine pappillomavirus, and the like (see, e.g., Co et al. (1992) *J. Immunol.* 1458: 1149).

An additional aspect of the present invention is a kit for the detection of a human PTCH2 gene or polypeptide comprising in a container a molecule selected from the group consisting of a nucleic acid, a polypeptide or a protein or an antibody according to the invention. Further suitable components of such a kit are easily determined by someone skilled in this field as are the conditions for the use thereof.

Further, the invention also realtes to the use of a nucleic acid selected from the group consisting of SEQ ID NOS: 2–4 and SEQ ID NO: 5 in gene therapy. In addition to said specifically disclosed sequences, any one of the herein disclosed exons may be used to this end. For a review of gene therapy procedures, see Anderson, *Science* (1992) 256:808–813; Nabel and Felgner (1993) *TIBTECH* 11: 211–217; Mitani and Caskey (1993) *TIBTECH* 11: 162–166; Mulligan (1993) *Science* 926–932; Dillon (1993) *TIBTECH* 11: 167–175; Miller (1992) *Nature* 357: 455–460; Van Brunt (1988) *Biotechnology* 6(10): 1149–1154; Vigne (1995) *Restorative Neurology and Neuroscience* 8: 35–36; Kremer and Perricaudet (1995) *British Medical Bulletin* 51(1) 31–44; Haddada et al. (1995) in *Current Topics in Microbiology and Immunology* Doerfler and Böhm (eds) Springer-Verlag, Heidelberg Germany; and Yu et al., *Gene Theraphy* (1994) 1:13–26.

Delivery of the gene or genetic material into the cell is the first critical step in gene therapy treatment of disease. A large number of delivery methods are well known to those of skill in the art. Such methods include, for example liposome-based gene delivery (Debs and Zhu (1993) WO 93/24640; Mannino and Gould-Fogerite (1988) *BioTechniques* 6(7): 682–691; Rose U.S. Pat. No. 5,279,833; Brigham (1991) WO 91/06309; and Felgner et al. (1987) *Proc. Natl. Acad. Sci. USA* 84: 7413–7414), and replication-defective retroviral vectors harboring a therapeutic polynucleotide uence as part of the retroviral genome (see, e.g., Miller et al. (1990) *Mol. Cell. Biol.* 10:4239 (1990; Kolberg (1992) *J. NIH Res.* 4:43, and Cornetta et al. *Hum. Gene Ther.* 2:215 (1991)). Widely used retroviral vectors include those based upon nurine leukemia virus (MuLV), gibbon ape leukemia virus (GaLV), Simian Immuno deficiency virus (SIV), human immuno deficiency virus (HIV), and combinations thereof See, e.g., Buchscher et al. (1992) *J. Virol.* 66 (5) 2731–2739; Johann et al. (1992) *J. Virol.* 66 (5):1635–1640 (1992); Sommerfelt et al., (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental*

Immunology, Third Edition Paul (ed) Raven Press, Ltd., New York and the references therein, and Yu et al., Gene Therapy (1994) supra).

The present invention may also be used in the pharmaceutical industry. For example, it will provide information that eventually may enable cells from fetal tissue, which may the be transplanted into patients suffering from e.g. Parkinson's disease or cancer, such as BCC. (For a brief review of methods of drug delivery, see Langer 249:1 527–1533 (1990), Remington's Pharmaceutical Sciences, Mack Publishing Company, Philadelphia, Pa., 17$^{th}$ ed. (1985) etc.)

DETAILED DESCRIPTION OF THE DRAWINGS

FIG. 1 shows the genomic sequence of SEQ ID NO:5, wherein exons and introns are designated in the genomic sequence of the present human patched 2 gene. However, exons 12a and 12b discussed above are not specifically shown in FIG. 1, but is instead disclosed as the separate sequences SEQ ID NO:3 and SEQ ID NO:4, respectively. FIG. 2A discloses an amino acid sequence comparison of the human PTCH2(residues 1–633 of SEQ ID NO:1)(upper lines) and PTCH1(residues 1–699 of SEQ ID NO:6) (lower lines) sequences. Vertical lines indicate identical amino acids, while dots similar amino acids. The PTCH2 sequence presented is composed of the original cDNA clones and of the products of the 5' RACE analysis.

FIG. 2B is a representation of the alternative splicing events (SEQ ID NOS:7, 8, 9, 10, 11, 12, 13, 14, 15 and 16) that result in different C-termini. In the parotid gland and the colon, the penultimate and the last exon are canonically joined together. In fetal brain however the penultimate exon with part of the 3' intron functions as the terminal exon. The intronic sequence is shown by small letters with the flanking exonic by capital letters. Above the nucleotide sequence, the deduced amino acid sequence is shown, and below is the corresponding sequence of the mouse Ptch2. The conserved intronic dinucleotides are shown by bold letters and the termination signals are indicated by asterisks. Note the absence of conservation of the position of the termination codons between the mouse and human PTCH2 sequences. The putative polyadenylation signals are also shown in this diagram. The genomic organization was obtained by analyzing BAC clones encompassing the PTCH2 gene.

Figure 2C:
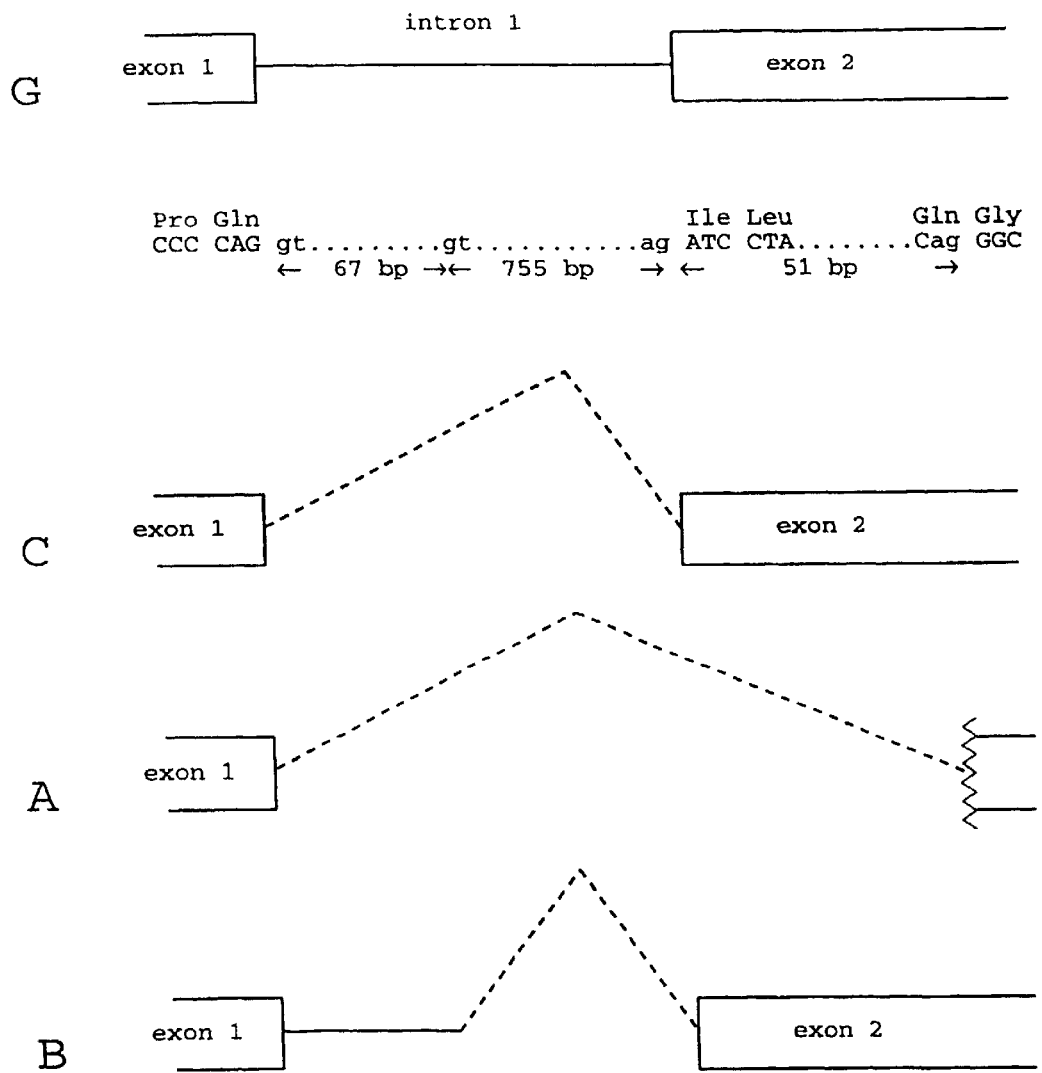
FIG. 2C is a representation of the different variations of spliced transcipts encompassing exon 1 and exon 2 sequences.

FIG. 2C is a representation of the different variations of spliced transcipts encompassing exon 1 and exon 2 sequences. The canonical exons 1 and 2 are shown by boxes and the intron between them by a solid line. The GT and AG dinucleotides spanning the sequences that are used as introns in individual transcripts are indicated by small letters. G, Genomic structure, derived from sequencing segements of BAC clones encompassing the PTCH2 gene; C, Canonical transcript; A, Transcript A (the skipped exons 9 and 10 of this product are not shown in the diagram); B, Transcript B.

Figure 3:
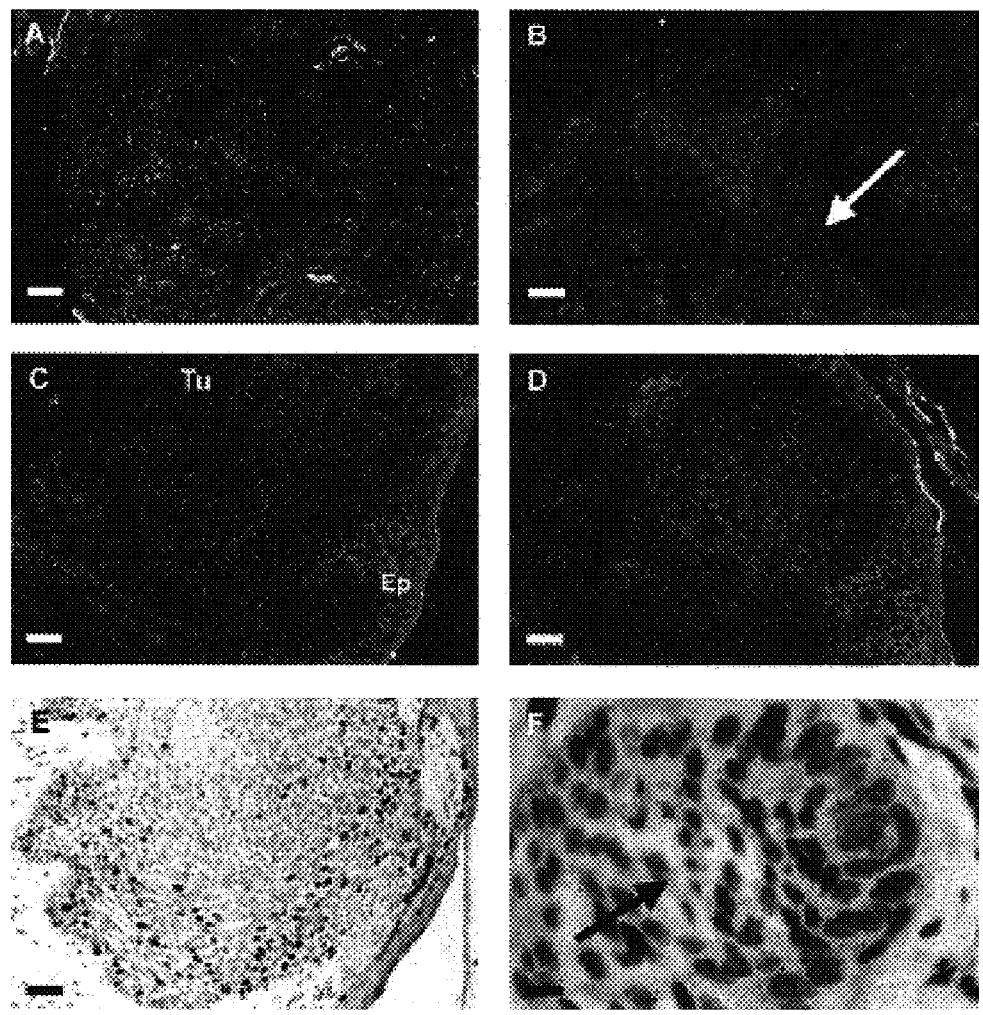
FIG. 3A is a dark-field photomicrograph of a BCC tumor hybridised with $^{35}$S-labeled antisense probe showing abundant signal for PTCH1 mRNA (light grains) in all BCC tumor cells.
FIG. 3B discloses PTCH2 mRNA overexpression in BCC and is in contrast mainly expressed in the basaloid cells in the periphery of the tumor nests.
FIG. 3C is another BCC showing a strong PTCH2 mRNA signal in the periphery of the tumor nest (Tu), wheras no signal is detected in epidermis (Ep).
FIG. 3D are sections of the same tumor (C) hybridised with the PTCH2 sense probe showed no signal.
FIG. 3E shows immunoreactivity for Ki-67.
FIG. 3F discloses how tumor nests under high power magnification demonstrate abundant PTCH2 mRNA signal (black grains) in the dark basaloid tumor cells and lower signal in the center (arrow).

FIG. 3A is a dark-field photomicrograph of a BCC tumor hybridised with $^{35}$S-labeled antisense probe showing abundant signal for PTCH1 mRNA (light grains) in all BCC tumor cells.

FIG. 3B discloses PTCH2 mRNA overexpression in BCC and is in contrast mainly expressed in the basaloid cells in the periphery of the tumor nests.

FIG. 3C is another BCC showing a strong PTCH2 mRNA signal in the periphery of the tumor nest (Tu), wheras no signal is detected in epidermis (Ep).

FIG. 3D are sections of the same tumor (C) hybridised with the PTCH2 sense probe showed no signal.

FIG. 3E shows immunoreactivity for Ki-67 (brown precipitate) seen in the periphery, in the cells that showed strong upregulation of PTCH2 mRNA.

FIG. 3F discloses tumor nests under high power magnification demonstrate abundant PATCH2 mRNA signal (black grains) in the dark basaloid tumor cells and lower signal in the center (arrow). Bars (A-E), 24 μm, and F, 6 μm.

EXPERIMENTAL

Materials and Methods

In the present context, a general reference is made to G. Zaphiropoulos et al., Cancer Res., vol. 59, p. 787–792, Feb. 15, 1999, disclosing useful methods in the present context. All references mentioned in the present application are hereby included herein by reference. The examples below are not intended to limit the scope of the invention but merely as an illusion.

The RACE analysis was performed essentially as described before (Zaphiropoulos, P. G. and Toftgård, R. (1996): "cDNA cloning of a novel WD repeat protein mapping to the 9q22.3 chromosomal region", DNA Cell Biol. 15, 1049–1056) using the Marathon kit (Promega). The primer sequences used for RACE are available upon request.

The PTCH2, 35S-labeled RNA probes used for the in situ hybridisations, that were performed as previously described (Undén et al., (1997), supra), corresponded to positions 218 to 437 and 838 to 920 in the PTCH2 sequence of SEQ ID NO:1.

Results and Discussion

In order to identify additional components of the PTCH (SHH cascade of signalling events, the Incyte LifeSeq™ database (Incyte Pharmaceuticals Inc., Palo Alto, Calif., USA) was searched using PTCH sequences. In addition to clones representing the PTCH cDNA, two nearly identical cDNAs were identified, from the parotid gland and the colon, that contained sequences similar to, but distinct from, the 3' end of PTCH. By 5' RACE analysis using fetal brain cDNAs additional sequence information from these transcripts (termed PTCH2) and corresponding to a fill length cDNA, was obtained (FIG. 2A). PTCH2 is 57% identical to PTCH1, with a significantly variable region present between the transmembrane domains 6 and 7, and 91% identical to the recently published mouse Ptch2 sequence (Motoyama, J., Takabatake, T., Takeshina, K. and Hui, C. (1998): "Ptch2, a second mouse Patched gene is co-expressed with Sonic hedgehog", Nature Genet. 18, 104–106). In similarity with the mouse gene, PTCH2 lacks the C-terminal extension present in human, mouse and chicken PTCH1 (Goodrich, L. V., Johnson, R. L., Milenkovic, L., McMahon, J. A., and Scott, M. P. (1996): "Conservation of the hedgehog/patched signalling pathway from flies to mice: Induction of a mouse patched gene by Hedgehog", Genes Dev. 10, 301–312, Marigo, V., Scott, M. P., Johnson, R. L., Goodrich, L. V. and Tabin, C. J. (1996): "Conservation in hedgehog signalling: Induction of a chicken patched homolog by Sonic hedgehog in the developing limb", Development 122, 1225–1233). However, according to the present invention, it has been shown that the human PTCH2 cDNA terminates 36 amino acids earlier that the mouse Ptch2 sequence. Moreover, when 3' RACE was perfomed from fetal brain, an alternate C-terminal region was identified. This had a high structural similarity with the mouse Ptch2 C-terminal sequence and originates from the genomic region that links the last two exons of PTCH2 (FIG. 2B). Therefore, in these alternatively spliced transcripts, the penultimate exon with a segment of the contiguous 3' intron serves as the terminal exon.

Moreover the human and mouse transcripts differed in the position of the termination signals (the human sequence is 21 amino acids longer), suggesting a non-conserved, species-specific function of this alternate C-terminal domain. The finding of two possible C-terminal regions for PTCH2 is intriguing and implies a role of this phenomenon in modulating signalling. Additional alternatively spliced transcripts were also identified by the RACE analysis (FIG. 2C). Transcript A lacks the sequence that corresponds to exons 9 and 10 of PTCH1 (preliminary comparisons of the intron exon junctions of PTCH2 with PTCH1 indicate a similar genomic organization), with the open reading frame being retained at the exon 8 to exon 11 junction. Exons 9 and 10 code for the last part of the first extracellular loop and for transmembrane domains 2 and 3 in the putative structure of the PTCH1 protein. Furthermore this transcript also lacks a 5' segment of the canonical exon 2, due to the use of an alternative 3' splice site present in this exon, with the open reading frame being maintained. The functional consequence of this alternative splicing is not yet known, but it is interesting to note that the extracellular loops in PTCH1 are presumed to be involved in binding of the ligand SHH (Marigo et al., (1996), Nature 384, supra; Stone et al., (1996), Nature 384, supra) and that insertion of a neocassette in intron 9 of the mouse PTCH1 gene is associated with a severe phenotype (Hahn, H., Wojnowski, L., Zimmer, A. M., Hall, J., Miller, G. and Zimmer, A. (1998): "Rhabdomyosarcomas and radiation hypersensitivity in a mouse model of Gorlin syndrome", Nature Med. 4, 619–622). Furthermore, exons 9 and 10 encode part of a putative sterol sensing domain (Osborne, T. F. and Rosenfeld, J. M. (1998): "Related membrane domains in proteins of sterol sensing and cell signalling provide a glimpse of treasures still buried within the dynamic realm of intracellular metabolic regulation", Curr. Opin. Lipidol. 9, 137–140, also found in PTCH1, and which has recently been implicated in mediating the potent modulating effect of cholesterol on SHH/PTCH signalling (Cooper, M. K, Porter, J. A., Young, K. E., and Beachy, P. A. (1998): "Teratogen-mediated inhibition of target tissue response to Shh signalling", Science 280, 1603–1607). Thus, if PTCH2 also serves as a receptor for SHH and/or related factors, the receptor form lacking exons 9 and 10 may show altered signalling properties. Transcript B contains additional sequences between canonical exons 1 and 2, that originate from the 5' end of intron 1. The open reading frame that includes the initiator metionine of exon 1 is not maintained in this transcript, suggesting that, if this transcript is functional, either the methionine in exon 2 or non-methionine codons are used in order to produce a protein product, in similarity to what has been proposed for the alternative spliced products of human PTCH1 (Hahn et al., Cell 85, supra). By radiation hybrid mapping the PTCH2 gene was localized to the short arm of chromosome 1, in difference to PTCH1 residing on chromosome 9q22.3.

The mouse and zebrafish homologs of PTCH2 have been reported to be expressed in a partly overlapping pattern with PTCH1 during embryonic development and to be induced by SHH (Motoyama et al., (1998) Nature Genet. 18, supra, Concordet, J. P., Lewis, K. E., Moore, J. W., Goodrich, L. V., Johnson, R. L., Scott, M. P., and Ingham, P. W. (1996): "Spatial regulation of a zebrafish patched homologue reflects the roles of sonic hedgehog and protein kinase A in a neural tube and somite patterning", Development 122, 2835–2846), implicating a role in this signalling pathway. We were with this background interested to analyze the expression of PTCH2 in BCCs which show consistent upregulation of PTCH1 in all tumor cells (Undén et al., (1997) Cancer res. 57, supra). In situ hybridisation was performed on six familial and four sporadic BCCs of different histological subtypes. A strong positive signal for PTCH2 mRNA was observed exclusively in the tumor cells of all BCCs. Notably, the signal was consistently stronger in the palisading peripheral cells of the tumor nests (FIG. 2). These cells also showed a positive immunostaining for the cell proliferation marker, Ki-67.

The finding that in BCCs having frequent mutations in the PTCH1 gene, the expression of the PTCH2 mRNAs is upregulated, tightly links the novel PTCH2 according to the invention with the PTCH/SHH cascade of signalling events. It is therefore likely that PTCH2 represents a target gene of this pathway which is under the negative regulation of PTCH1, precisely as PTCH1 itself Moreover this observation strongly suggests that PTCH2 has functions distinct from PTCH1 since upregulation of PTCH2 expression appears unable to compensate for inactive PTCH1 protein. This conclusion is also supported by the early embryonic lethality seen in PTCH1 (−/−) mice 5,13) and the lack of genetic heterogeneity in Gorlin syndrome. However, whether PTCH2 may block the constitutive signalling of SMO, or could act as an additional SHH receptor, possible dependent on alternative splicing, remains as the subject of further experimentation.

We claim:

1. An isolated nucleic acid consisting of the sequence of SEQ ID NO: 5.

2. An isolated nucleic acid encoding a protein consisting of SEQ ID NO: 1.

3. A composition, comprising the nucleic acid according to claim 1 or claim 2.

4. A vector comprising a nucleic acid according to claim 1 or claim 2.

5. An isolated recombinant cell comprising a vector according to claim 4.

6. A kit for the detection of a human PTCH2 gene comprising in a container a nucleic acid according to claim 1 or claim 2.

* * * * *

SEQUENCE LISTING

```
<160> NUMBER OF SEQ ID NOS: 16

<210> SEQ ID NO 1
<211> LENGTH: 1146
<212> TYPE: PRT
<213> ORGANISM: Homo sapiens

<400> SEQUENCE: 1

Met Thr Arg Ser Pro Pro Leu Arg Glu Leu Pro Pro Ser Tyr Thr Pro
1               5                   10                  15

Pro Ala Arg Thr Ala Ala Pro Gln Ile Leu Ala Gly Ser Leu Lys Ala
            20                  25                  30
```

-continued

```
Pro Leu Trp Leu Arg Ala Tyr Phe Gln Gly Leu Leu Phe Ser Leu Gly
        35                  40                  45

Cys Gly Ile Gln Arg His Cys Gly Lys Val Leu Phe Leu Gly Leu Leu
        50                  55                  60

Ala Phe Gly Ala Leu Ala Leu Gly Leu Arg Met Ala Ile Ile Glu Thr
65                  70                  75                  80

Asn Leu Glu Gln Leu Trp Val Glu Val Gly Ser Arg Val Ser Gln Glu
                85                  90                  95

Leu His Tyr Thr Lys Glu Lys Leu Gly Glu Ala Ala Tyr Thr Ser
                100                 105                 110

Gln Met Leu Ile Gln Thr Ala Arg Gln Glu Gly Glu Asn Ile Leu Thr
        115                 120                 125

Pro Glu Ala Leu Gly Leu His Leu Gln Ala Ala Leu Thr Ala Ser Lys
        130                 135                 140

Val Gln Val Ser Leu Tyr Gly Lys Ser Trp Asp Leu Asn Lys Ile Cys
145                 150                 155                 160

Tyr Lys Ser Gly Val Pro Leu Ile Glu Asn Gly Met Ile Glu Arg Met
                165                 170                 175

Ile Glu Lys Leu Phe Pro Cys Val Ile Leu Thr Pro Leu Asp Cys Phe
        180                 185                 190

Trp Glu Gly Ala Lys Leu Gln Gly Gly Ser Ala Tyr Leu Pro Gly Arg
        195                 200                 205

Pro Asp Ile Gln Trp Thr Asn Leu Asp Pro Glu Gln Leu Leu Glu Glu
        210                 215                 220

Leu Gly Pro Phe Ala Ser Leu Glu Gly Phe Arg Glu Leu Leu Asp Lys
225                 230                 235                 240

Ala Gln Val Gly Gln Ala Tyr Val Gly Arg Pro Cys Leu His Pro Asp
                245                 250                 255

Asp Leu His Cys Pro Pro Ser Ala Pro Asn His His Ser Arg Gln Ala
                260                 265                 270

Pro Asn Val Ala His Glu Leu Ser Gly Cys His Gly Phe Ser His
        275                 280                 285

Lys Phe Met His Trp Gln Glu Leu Leu Leu Gly Gly Met Ala Arg
        290                 295                 300

Asp Pro Gln Gly Glu Leu Leu Arg Ala Glu Ala Leu Gln Ser Thr Phe
305                 310                 315                 320

Leu Leu Met Ser Pro Arg Gln Leu Tyr Glu His Phe Arg Gly Asp Tyr
                325                 330                 335

Gln Thr His Asp Ile Gly Trp Ser Glu Gln Ala Ser Thr Val Leu
                340                 345                 350

Gln Ala Trp Gln Arg Arg Phe Val Gln Leu Ala Gln Glu Ala Leu Pro
        355                 360                 365

Glu Asn Ala Ser Gln Gln Ile His Ala Phe Ser Ser Thr Thr Leu Asp
        370                 375                 380

Asp Ile Leu His Ala Phe Ser Glu Val Ser Ala Ala Arg Val Val Gly
385                 390                 395                 400

Gly Tyr Leu Leu Met Leu Ala Tyr Ala Cys Val Thr Met Leu Arg Trp
                405                 410                 415

Asp Cys Ala Gln Ser Gln Gly Ser Val Gly Leu Ala Gly Val Leu Leu
        420                 425                 430

Val Ala Leu Ala Val Ala Ser Gly Leu Gly Leu Cys Ala Leu Leu Gly
435                 440                 445

Ile Thr Phe Asn Ala Ala Thr Thr Gln Val Leu Pro Phe Leu Ala Leu
```

-continued

```
            450                 455                 460
Gly Ile Gly Val Asp Asp Val Phe Leu Leu Ala His Ala Phe Thr Glu
465                 470                 475                 480

Ala Leu Pro Gly Thr Pro Leu Gln Glu Arg Met Gly Glu Cys Leu Gln
                485                 490                 495

Arg Thr Gly Thr Ser Val Val Leu Thr Ser Ile Asn Asn Met Ala Ala
                500                 505                 510

Phe Leu Met Ala Ala Leu Val Pro Ile Pro Ala Leu Arg Ala Phe Ser
            515                 520                 525

Leu Gln Ala Ala Ile Val Val Gly Cys Thr Phe Val Ala Val Met Leu
530                 535                 540

Val Phe Pro Ala Ile Leu Ser Leu Asp Leu Arg Arg Arg His Cys Gln
545                 550                 555                 560

Arg Leu Asp Val Leu Cys Cys Phe Ser Ser Pro Cys Ser Ala Gln Val
                565                 570                 575

Ile Gln Ile Leu Pro Gln Glu Leu Gly Asp Gly Thr Val Pro Val Gly
                580                 585                 590

Ile Ala His Leu Thr Ala Thr Val Gln Ala Phe Thr His Cys Glu Ala
                595                 600                 605

Ser Ser Gln His Val Val Thr Ile Leu Pro Pro Gln Ala His Leu Val
        610                 615                 620

Pro Pro Pro Ser Asp Pro Leu Gly Ser Glu Leu Phe Ser Pro Gly Gly
625                 630                 635                 640

Ser Thr Arg Asp Leu Leu Gly Gln Glu Glu Thr Arg Gln Lys Ala
                645                 650                 655

Ala Cys Lys Ser Leu Pro Cys Ala Arg Trp Asn Leu Ala His Phe Ala
                660                 665                 670

Arg Tyr Gln Phe Ala Pro Leu Leu Gln Ser His Ala Lys Ala Ile
                675                 680                 685

Val Leu Val Leu Phe Gly Ala Leu Leu Gly Leu Ser Leu Tyr Gly Ala
            690                 695                 700

Thr Leu Val Gln Asp Gly Leu Ala Leu Thr Asp Val Val Pro Arg Gly
705                 710                 715                 720

Thr Lys Glu His Ala Phe Leu Ser Ala Gln Leu Arg Tyr Phe Ser Leu
                725                 730                 735

Tyr Glu Val Ala Leu Val Thr Gln Gly Gly Phe Asp Tyr Ala His Ser
                740                 745                 750

Gln Arg Ala Leu Phe Asp Leu His Gln Arg Phe Ser Ser Leu Lys Ala
            755                 760                 765

Val Leu Pro Pro Pro Ala Thr Gln Ala Pro Arg Thr Trp Leu His Tyr
770                 775                 780

Tyr Arg Asn Trp Leu Gln Gly Ile Gln Ala Ala Phe Asp Gln Asp Trp
785                 790                 795                 800

Ala Ser Gly Arg Ile Thr Arg His Ser Tyr Arg Asn Gly Ser Glu Asp
                805                 810                 815

Gly Ala Leu Ala Tyr Lys Leu Leu Ile Gln Thr Gly Asp Ala Gln Glu
            820                 825                 830

Leu Leu Asp Phe Ser Gln Leu Thr Thr Arg Lys Leu Val Asp Arg Glu
            835                 840                 845

Gly Leu Ile Pro Pro Glu Leu Phe Tyr Met Gly Leu Thr Val Trp Val
        850                 855                 860

Ser Ser Asp Pro Leu Gly Leu Ala Ala Ser Gln Ala Asn Phe Tyr Pro
865                 870                 875                 880
```

-continued

```
Pro Pro Pro Glu Trp Leu His Asp Lys Tyr Asp Thr Thr Gly Glu Asn
            885                 890                 895
Phe Arg Ile Pro Pro Ala Gln Pro Leu Glu Phe Ala Gln Phe Pro Phe
            900                 905                 910
Leu Leu Arg Gly Leu Gln Lys Thr Ala Asp Phe Val Glu Ala Ile Glu
            915                 920                 925
Gly Ala Arg Ala Ala Cys Ala Glu Ala Gly Gln Ala Gly Val His Ala
            930                 935                 940
Tyr Pro Ser Gly Ser Pro Phe Leu Phe Trp Glu Gln Tyr Leu Gly Leu
945                 950                 955                 960
Arg Arg Cys Phe Leu Leu Ala Val Cys Ile Leu Leu Val Cys Thr Phe
            965                 970                 975
Leu Val Cys Ala Leu Leu Leu Asn Pro Trp Thr Ala Gly Leu Ile
            980                 985                 990
Val Leu Val Leu Ala Met Met Thr  Val Glu Leu Phe Gly  Ile Met Gly
            995                1000                1005
Phe Leu Gly Ile Lys Leu Ser  Ala Ile Pro Val Val  Ile Leu Val
    1010                1015                1020
Ala Ser Val Gly Ile Gly Val  Glu Phe Thr Val His  Val Ala Leu
    1025                1030                1035
Gly Phe Leu Thr Thr Gln Gly  Ser Arg Asn Leu Arg  Ala Ala His
    1040                1045                1050
Ala Leu Glu His Thr Phe Ala  Pro Val Thr Asp Gly  Ala Ile Ser
    1055                1060                1065
Thr Leu Leu Gly Leu Leu Met  Leu Ala Gly Ser His  Phe Asp Phe
    1070                1075                1080
Ile Val Arg Tyr Phe Phe Ala  Ala Leu Thr Val Leu  Thr Leu Leu
    1085                1090                1095
Gly Leu Leu His Gly Leu Val  Leu Leu Pro Val Leu  Leu Ser Ile
    1100                1105                1110
Leu Gly Pro Pro Pro Glu Val  Ile Gln Met Tyr Lys  Glu Ser Pro
    1115                1120                1125
Glu Ile Leu Ser Pro Pro Ala  Pro Gln Gly Gly Gly  Leu Arg Pro
    1130                1135                1140
Glu Glu Ile
    1145

<210> SEQ ID NO 2
<211> LENGTH: 3453
<212> TYPE: DNA
<213> ORGANISM: Homo sapiens

<400> SEQUENCE: 2
atccccgcca gcatgactcg atcgccgccc ctcagagagc tgcccccgag ttacacaccc      60
ccagctcgaa ccgcagcacc ccagatccta gctgggagcc tgaaggctcc actctggctt     120
cgtgcttact ccagggcct  gctcttctct ctgggatgcg ggatccagag acattgtggc     180
aaagtgctct ttctgggact gttggccttt ggggccctgg cattaggtct ccgcatggcc     240
attattgaga caaacttgga acagctctgg gtagaagtgg gcagccgggt gagccaggag     300
ctgcattaca ccaaggagaa gctgggggag gaggctgcat acacctctca gatgctgata     360
cagaccgcac gccaggaggg agagaacatc ctcacacccg aagcacttgg cctccacctc     420
caggcagccc tcactgccag taaagtccaa gtatcactct atgggaagtc ctgggatttg     480
```

-continued

```
aacaaaatct gctacaagtc aggagttccc cttattgaaa atggaatgat tgagcggatg      540
attgagaagc tgtttccgtg cgtgatcctc accccctcg actgcttctg ggagggagcc       600
aaactccaag ggggctccgc ctacctgccc ggccgcccgg atatccagtg gaccaacctg      660
gatccagagc agctgctgga ggagctgggt ccctttgcct cccttgaggg cttccgggag      720
ctgctagaca aggcacaggt gggccaggcc tacgtggggc ggccctgtct gcaccctgat      780
gacctccact gcccacctag tgccccaac catcacagca ggcaggctcc caatgtggct       840
cacgagctga gtggggctg ccatggcttc tcccacaaat tcatgcactg gcaggaggaa      900
ttgctgctgg gaggcatggc cagagacccc aaggagagc tgctgagggc agaggccctg      960
cagagcacct tcttgctgat gagtccccgc cagctgtacg agcatttccg gggtgactat     1020
cagacacatg acattggctg gagtgaggag caggccagca cagtgctaca agcctggcag     1080
cggcgctttg tgcagctggc ccaggaggcc ctgcctgaga acgcttccca gcagatccat     1140
gccttctcct ccaccaccct ggatgacatc ctgcatgcgt tctctgaagt cagtgctgcc     1200
cgtgtggtgg gaggctatct gctcatgctg gcctatgcct gtgtgaccat gctgcggtgg     1260
gactgcgccc agtcccaggg ttccgtgggc cttgccgggg tactgctggt ggccctggcg     1320
gtggcctcag gccttgggct ctgtgccctg ctcggcatca ccttcaatgc tgccactacc     1380
caggtgctgc ccttcttggc tctgggaatc ggcgtggatg acgtattcct gctggcgcat     1440
gccttcacag aggctctgcc tggcacccct ctccaggagc gcatgggcga gtgtctgcag     1500
cgcacgggca ccagtgtcgt actcacatcc atcaacaaca tggccgcctt cctcatggct     1560
gccctcgttc ccatccctgc gctgcgagcc ttctccctac aggcggccat agtggttggc     1620
tgcacctttg tagccgtgat gcttgtcttc ccagccatcc tcagcctgga cctacgcgg      1680 cgccactgcc agcgccttga tgtgctctgc tgcttctcca gtccctgctc tgctcaggtg     1740
attcagatcc tgccccagga gctgggggac gggacagtac cagtgggcat tgcccacctc     1800
actgccacag ttcaagcctt tacccactgt gaagccagca gccagcatgt ggtcaccatc     1860
ctgcctcccc aagcccacct ggtgccccca ccttctgacc cactgggctc tgagctcttc     1920
agccctggag ggtccacacg ggaccttcta ggccaggagg aggagacaag gcagaaggca     1980
gcctgcaagt ccctgccctg tgcccgctgg aatcttgccc atttcgcccg ctatcagttt     2040
gccccgttgc tgctccagtc acatgctaag gccatcgtgc tggtgctctt tggtgctctt     2100
ctgggcctga gcctctacgg agccaccttg gtgcaagacg gcctggccct gacggatgtg     2160
gtgcctcggg gcaccaagga gcatgccttc ctgagcgccc agctcaggta cttctccctg     2220
tacgaggtgg ccctggtgac ccaggtggc tttgactacg cccactccca acgcgccctc      2280
tttgatctgc accagcgctt cagttccctc aaggcggtgc tgcccccacc ggccacccag     2340 gcacccccgca cctggctgca ctattaccgc aactggctac agggaatcca ggctgccttt     2400
gaccaggact gggcttctgg gcgcatcacc cgccactcgt accgcaatgg ctctgaggat     2460
ggggccctgg cctacaagct gctcatccag actggagacg cccaggagct tctggatttc     2520
agccagctga ccacaaggaa gctggtggac agagagggac tgattccacc cgagctcttc     2580
tacatggggc tgaccgtgtg ggtgagcagt gaccccctgg gtctggcagc ctcacaggcc     2640
aacttctacc cccacctcc tgaatggctg cacgacaaat acgacaccac ggggagaac       2700 tttcgcatcc cgccagctca gcccttggag tttgcccagt tccccttcct gctgcgtggc     2760
ctccagaaga ctgcagactt tgtggaggcc atcgaggggg cccggcagc atgcgcagag      2820 gccggccagg ctggggtgca cgcctacccc agcggctccc ccttcctctt ctgggaacag     2880
```

```
tatctgggcc tgcggcgctg cttcctgctg gccgtctgca tcctgctggt gtgcactttc    2940
ctcgtctgtg ctctgctgct cctcaacccc tggacggctg gcctcatagt gctggtcctg    3000
gcgatgatga cagtggaact ctttggtatc atgggtttcc tgggcatcaa gctgagtgcc    3060
atccccgtgg tgatccttgt ggcctctgta ggcattggcg ttgagttcac agtccacgtg    3120
gctctgggct tcctgaccac ccagggcagc cggaacctgc gggccgccca tgcccttgag    3180
cacacatttg cccccgtgac cgatggggcc atctccacat tgctgggtct gctcatgctt    3240
gctggttccc actttgactt cattgtaagg tacttctttg cggcgctgac agtgctcacg    3300
ctcctgggcc tcctccatgg actcgtgctg ctgcctgtgc tgctgtccat cctgggcccg    3360
ccgccagagg tgatacagat gtacaaggaa agcccagaga tcctgagtcc accagctcca    3420
cagggaggcg ggcttaggcc cgaggagatc tag                                 3453

<210> SEQ ID NO 3
<211> LENGTH: 126
<212> TYPE: DNA
<213> ORGANISM: Homo sapiens

<400> SEQUENCE: 3
gagcgcatgg gcgagtgtct gcagcgcacg ggcaccagtg tcgtactcac atccatcaac     60
aacatggccg ccttcctcat ggctgccctc gttcccatcc ctgcgctgcg agccttctcc    120
ctacag                                                               126

<210> SEQ ID NO 4
<211> LENGTH: 119
<212> TYPE: DNA
<213> ORGANISM: Homo sapiens

<400> SEQUENCE: 4
gcggccatag tggttggctg caccttttgta gccgtgatgc ttgtcttccc agccatcctc     60
agcctggacc tacggcggcg ccactgccag cgccttgatg tgctctgctg cttctccag    119

<210> SEQ ID NO 5
<211> LENGTH: 12886
<212> TYPE: DNA
<213> ORGANISM: Homo sapiens

<400> SEQUENCE: 5
cgggtgaatc ccggcgccgc gccccggacc cgcagctccc tgcactcctc cctcccagcc     60
gctttaacac ccacaccccca cagtctctcc cacgsccgcg ccttggcggc cccactgaat    120
ccctacgcgg ggcccagcgg taccgggaga ccgggctagc ctatgggagc gcccagataa    180
cgcgggttgg gggcgcccgc gcccccatcc ccgccagcat gactcgatcg ccgcccctca    240
gagagctgcc cccgagttac acaccccccag ctcgaaccgc agcacccccag gtgagtagag    300 ggggagctgg aagaaggaag agagcggagc caggtctgtc actcgggcct ctgcaaggtt    360
tgtgatgtct tgaagtgccg agtgtcatta gatgtctgaa ggcaagtgag agccagcacc    420
gcaagcaagt tgtgcgtgtg tgtcggtgtg tctgtgccgg tgtctcctca tcgtctggcc    480
agtgagaatg aatgtctgtg ggttcacctc tgtgtccacc cgacgacagg tgtgtgtaca    540
tatgtatcct gctctcagaa aatgggccta tgccgccggg cgcggtgact cacgcctgta    600
atcccaacac tggaggctg aggcaggcag attacctgag gtcaggagtt cgagaccagc    660
caggccaaca tggggaaact ctgtctctac taaaaataaa aattagcagg gcgtggtggc    720
```

-continued

```
gggcgcctgt agtcccaact actcgggagg ctgaggcagg agaatctctt gaacctggga    780
ggcggaggtt gcagtcaagc cgagatcaca ccactgcact ccagccaggg caacagagcg    840
agatgcgtct caaaaaaaaa aaaaaaaaaa aaaaggagag aaaacaaaaa gaaaagaaag    900
gaaaataggc ctatgccttc ctcaggtgtg tgctggggat ggtgggtgtt acatcttcca    960
agtctgggcc tgtgtctgtg ttggtgctcc ctgtcccaca tccagaaatc aagaagcgag   1020
ggctgggcag cagatataca gggtgagaag ggaaggattt catgcattgt tacagtgatg   1080
cctggctgac ccttctcttt ccatcccaga tcctagctgg gagcctgaag gctccactct   1140
ggcttcgtgc ttacttccag ggcctgctct tctctctggg atgcgggatc cagagacatt   1200
gtggcaaagt gctctttctg ggactgttgg cctttggggc cctggcatta ggtctccgca   1260
tggccattat tgagacaaac ttggaacagc tctgggtaga aggtaagttg tggacactgg   1320
ccatagctgc tcaggtatgg tgagcccaag acaagaacgg ggtgaggagc tggctactga   1380
gctctagcag gcctggccct ggggctggag ggtcacctgc tggccagagt cctacacctg   1440
ggcatctagg aacaccgttc cctcccacaa ccataaatgg acatctgcag atgttagacc   1500
ttgtgaattg ggtgtataga atatttgtct gtgattttgc ttaagcccta gaccacacaa   1560
gaaatccgca gagccacaca accgaggctt ctccacttcc ctggcagagc tccaggaccc   1620
agaagcctgg ggagtcggcc tgggccatga ccaggccctc agggataagg cagggactcc   1680
tctctgccgc acctctccca cttgtctggg gaggcctcag agttagaagc ccccttcgca   1740
agttctgacc cgcctaggcc ctttccccccc cagctttctc tgtttgctct ggcagtgggc   1800
agccgggtga gccaggagct gcattacacc aaggagaagc tgggggagga ggctgcatac   1860
acctctcaga tgctgataca gaccgcacgc caggagggag agaacatcct cacacccgaa   1920
gcacttggcc tccacctcca ggcagccctc actgccagta aagtccaagt atcactctat   1980
gggaaggtga gtcggctgag gcccctgagc agctgggggc gaggcgtgct gtggggttc    2040
tggagtggga atcccttct tctgctgatc tcctatgccc ctggctattg cagtcctggg    2100
atttgaacaa aatctgctac aagtcaggag ttcccctatt tgaaaatgga atgattgagc    2160
gggtaagtgt cctgagaggg agtagaggca gaacttttc tgtagcgtgg gaggactcag    2220
agaccgagca agccccacag cctgcaatct gccccttaa aactaaggag ggggattgca    2280
gagggcatcc tacaaaggtt gtggggcagg actgacgtgg cccgggtat ccctggcaga    2340
tgattgagaa gctgtttccg tgcgtgatcc tcacccccct cgactgcttc tgggagggag    2400
ccaaactcca aggggctcc gcctacctgc cgtgagtgcc actcctgggg ccctgcttca    2460
tctcccgctg gggactctcc cagcagaaag gagggtctg gggaatgagg atgatcaaaa    2520
ccttaccaag gtcctaatta cctcccaggc caggaacaga gagcatgggc ttccccaagg   2580
ctctctccac atcctccttc tctttccctc tcaaggaagg aagacctgac ttatttacac   2640
aaaactaaac acaaagatct gtaagatctg agcaaaggag aaaagatcc ccacaaagag    2700
gctttgctgg gggaaattac ctaggtgttt gctaagccat tgcccaggcc agaaagaaaa   2760
cctgctacag gcatgtgcct gctggttgta tattagaacc aagcacacag cttggtaagg   2820
aactcagtgg ggccttctctg ggccctttct atgtattagg taaccctgcc ctgatattcg   2880
tctcagcccc ttgtactctt ctacagctca ctgtagcacc ctggtgggcc catgcagcct   2940
ggcagttctg agaagctgag gcttgcacac cctccatatg aaggacaaa tcggcagata   3000
agaggagggt ggggtacagc atggcgcccc agcagcagtt tggagcctgg gttttcgtcc   3060
ctgacccctca ccaactatag gcttttccct cagcggccgc ccggatatcc agtggaccaa   3120
```

-continued

```
cctggatcca gagcagctgc tggaggagct gggtcccttt gcctcccttg agggcttccg    3180
ggagctgcta gacaaggcac aggtgggcca ggcctacgtg gggcggccct gtctgcaccc    3240
tgatgacctc cactgcccac ctagtgcccc aaccatcac agcaggcagg tgggttccaa     3300
ccaggtctgc cagggaaagg ctgttttcct tccctttccc ttcctcatac tcctgtgttc    3360
tgggggagct gactgctctg tgccctgacc ccccacttcc tggccattat taccctgctc   3420
ccacagtgcc aggcccccaa tgttccattc ccattcagtt atcctacgga gccctcaagt   3480
ggtatatatg aatccctttt cctttctca agcctagata aggctggact tcttttttt     3540
ttttttttg agtctcactc tgtcacccag gctggagtgc agtagttcga tcttggctca    3600
ctgcaacctc ggctcaagca attctcctgc cttagcctcc tgagtagctg ggattacagg   3660
tgcccaccac catgcccggc taatttttat tagcctccca aagtgctggg attacaggcg   3720
tgagccactg cgcctggcca aggctggact ttttatcaaa atagactaat acagggaaac   3780
taagaacaca gcaggtaagc atgaatatca tacctggttt cccaggtttc tttgtggccc   3840
tgcaaatgtg gtactttttt cagaatccgc cagttacacc agctcctccc agaagcctac   3900
ttccaggcct ctgcttcccc ttggggcttc ctgtctgcgg gatactagct gttcactcct   3960
gcagagcagt caagaggctc agaatagtta cctacactcc agccctactg agcttcatgg   4020
cagcgtggtt cctggaggtg aagcccagg gacactcagt tatccacggc cagggccttg    4080
agcattaacc cctcctgttc ccctccaggg ctcccaatgt ggctcacgag ctgagtgggg   4140
gctgccatgg cttctcccac aaattcatgc actggcagga ggaattgctg ctgggaggca   4200
tggccagaga cccccaagga gagctgctga ggtagggtct cctctgggag ttggtgaggg   4260
gactctgttc atgagaaccc atactgtaat gccaggcagc tctggcaaaa ggcccttcac   4320
atccctcacc aggtgtttgg gccagctctg accctggtt ctcccacacc cccaccaggg    4380
cagaggccct gcagagcacc ttcttgctga tgagtccccg ccagctgtac gagcatttcc   4440
ggggtgacta tcagacacat gacattggct ggagtgagga gcaggccagc acagtgctac   4500
aagcctggca gcgcgctttt gtgcaggtcg gtatggacaa ggacaagggg ggtgccctga   4560
ggccattccc tcctcctgcc ccctcctatc caccctgttt ctccagctgg cccaggaggc   4620
cctgcctgag aacgcttccc agcagatcca tgccttctcc tccaccaccc tggatgacat   4680
cctgcatgcg ttctctgaag tcagtgctgc ccgtgtggtg ggaggctatc tgctcatggt   4740
gggtcttgca cctggcacct tgccccccacc ccacctccaa ccagtgccca ccctgggagc   4800
ccctgagact gcccttttccc cccacagctg gcctatgcct gtgtgaccat gctgcggtgg   4860
gactgcgccc agtcccaggg ttccgtgggc cttgccgggg tactgctggt ggccctggcg   4920
gtggcctcag gccttgggct ctgtgccctg ctcggcatca ccttcaatgc tgccactacc   4980
caggtacgcc aggactgcag gcagactca gtgccagtca ccaggcttca cgggtcctca    5040
gctgcccgct cctctgcccc tccaggtgct gcccttcttg gctctgggaa tcggcgtgga   5100
tgacgtattc ctgctggcgc atgccttcac agaggtctg cctggcaccc ctctccaggt    5160
ggggccttgt cccccagggc tcatctgagg cagctcagct tactggttaa gagcctcttg   5220
gttcaagtga ccctttgggct gctaatgaac ctcggtgcct cttgtcccca tctgtaaaca   5280
ggggaaataa tagtgctgtg tcctaagggt tattgtttgg atcagtgagg taactcaagt   5340
tgaatgctta gaacagccca tcatacgtac atggtaccca ataaatgcta gccactgtgt   5400
tatgactgcc ccacctctgc accccaagtt cctgagcctc cccttcactc cacttttgaca   5460
```

-continued

| | | | | |
|---|---|---|---|---|
| cggcccctcc | cttgtgacct | gagggcaggt | ccccactctg | tcctggcagg agcgcatggg | 5520 |
| cgagtgtctg | cagcgcacgg | gcaccagtgt | cgtactcaca | tccatcaaca acatggccgc | 5580 |
| cttcctcatg | gctgccctcg | ttcccatccc | tgcgctgcga | gccttctccc tacaggcggc | 5640 |
| catagtggtt | ggctgcacct | ttgtagccgt | gatgcttgtc | ttcccagcca tcctcagcct | 5700 |
| ggacctacgg | cggcgccact | gccagcgcct | tgatgtgctc | tgctgcttct ccaggtactg | 5760 |
| cgtgcgcccc | agccccttcc | tcccgtgacc | cacgccagcc | tgtcccctca ccagcatttc | 5820 |
| aaggcacaga | cctgtcatcc | actctctacc | tcttccagtc | cctgctctgc tcaggtgatt | 5880 |
| cagatcctgc | cccaggagct | ggggacggg | acagtaccag | tgggcattgc ccacctcact | 5940 |
| gccacagttc | aagcctttac | ccactgtgaa | gccagcagcc | agcatgtggt caccatcctg | 6000 |
| cctcccaag | cccacctggt | gccccacct | tctgacccac | tgggctctga gctcttcagc | 6060 |
| cctggagggt | ccacacggga | ccttctaggc | caggaggagg | agacaaggca gaaggcagcc | 6120 |
| tgcaagtccc | tgccctgtgc | ccgctggaat | cttgcccatt | tcgcccgcta tcagtttgcc | 6180 |
| ccgttgctgc | tccagtcaca | tgctaaggta | agactgggca | gagcagggca gagacttagc | 6240 |
| atctctgggc | ccagaagggc | agagagggct | tagtccactg | cctgaggggc tgggggcagc | 6300 |
| cctggggtct | ccagcttagt | tgctacatcc | cgcaggccat | cgtgctggtg ctctttggtg | 6360 |
| ctcttctggg | cctgagcctc | tacgagcca | ccttggtgca | agacgcctg gccctgacgg | 6420 |
| atgtggtgcc | tcgggcacc | aaggagcatg | ccttcctgag | cgcccagctc aggtacttct | 6480 |
| ccctgtacga | ggtggccctg | gtgacccagg | gtggctttga | ctacgcccac tcccaacgcg | 6540 |
| ccctctttga | tctgcaccag | cgcttcagtt | ccctcaaggc | ggtgctgccc ccaccggcca | 6600 |
| cccaggcacc | ccgcacctgg | ctgcactatt | accgcaactg | gctacagggt gagaggcgag | 6660 |
| gagacgggca | gggaggggtg | ctgcagggag | aaacgccctg | gggccaccag ctaatagaac | 6720 |
| cctatcctgg | tctcccccag | gaatccaggc | tgcctttgac | caggactggg cttctgggcg | 6780 |
| catcacccgc | cactcgaccg | caatggctct | gaggatgggg | ccctggccta caagctgctc | 6840 |
| atccagactg | gagacgccca | ggagcttctg | gatttcagcc | aggttgggag agggctggag | 6900 |
| gggtccacta | gtacagggc | tgcaggcctc | ctgggcccag | gccttcagcc ctctctgcct | 6960 |
| ctgcagctga | ccacaaggaa | gctggtggac | agagagggac | tgattccacc cgagctcttc | 7020 |
| tacatgggc | tgaccgtgtg | ggtgagcagt | gaccccctgg | gtctggcagc ctcacaggcc | 7080 |
| aacttctacc | ccccacctcc | tgaatggctg | cacgacaaat | acgacaccac ggggagaac | 7140 |
| tttcgcagtg | agtcttgggg | ggagctcggc | aagagcctca | gcctcgccca cacaagccct | 7200 |
| gagcctgagg | ccctgcccac | tctgccccgt | gctcaccgcc | ctgtccctct ccctcttctc | 7260 |
| ccttcccctc | ccctccacag | tcccgccagc | tcagcccttg | gagtttgccc agttccctt | 7320 |
| cctgctgcgt | ggcctccaga | agactgcaga | cttgtggag | gccatcgagg gggcccgggc | 7380 |
| agcatgcgca | gaggccggcc | aggctgggt | gcacgcctac | cccagcggct ccccccttcct | 7440 |
| cttctgggaa | cagtatctgg | gcctgcggcg | ctgcttcctg | ctggccgtct gcatcctgct | 7500 |
| ggtgtgcact | ttcctcgtct | gtgctctgct | gctcctcaac | ccctggacgg ctggcctcat | 7560 |
| agtgagtgct | tgcaggagtg | gggacagaga | cacccaccc | ttccctgccc agcctgtcat | 7620 |
| ccctcctgcc | aggagccctc | tgtgagccct | gtctccctca | ggtgctggtc ctggcgatga | 7680 |
| tgacagtgga | actctttggt | atcatggggtt | tcctgggcat | caagctgagt gccatccccg | 7740 |
| tggtgatcct | tgtggcctct | gtaggcattg | gcgttgagtt | cacagtccac gtggctctgg | 7800 |
| tgagcacggg | caccccgggg | agggaccaat | cagctgattc | agtattcaac acatattgtt | 7860 |

-continued

```
caagcccta ctatgtgcta ggtactattt aagaatttgg gctgggtgga cgtggtagct    7920
cattcctgta atcccagcac tttgggaggc cgaggcaggt ggatcacctg aggtcaggag    7980
ttcgaaacca gcctggccaa catggtgaaa ccctgtcttt actaaaaata caaaaaatta    8040
gccaggcgtg gtggcacatg ccagtaatcc cagctacttt ggaggctgag gcagaattgc    8100
ttgaacctgg gaggcgaagg ttgcagtgag ctgagatcgt gccattgcac tccagcctgg    8160
gcaacaagag tgaaactctc cgtctcaaaa aaaaaaaaa aaagaatttt gggctgggca    8220
cagtggctca tgcctgtaat tgggatgatg ctggggcatt ttgggaggcc aaggcaggcg    8280
gatcccctga agtcaggagt tcaagaccag cctggccaac attgcaaaac cccgtctcta    8340
ctgaaaatac aaaaattagc tgggcgtggt ggctcatgcc tgtaatccca gctactcagg    8400
aggctgaggc aggagaatta cttgaaccca ggaggcggag gttacagtga gctgagatca    8460
catcactgta ctccagcctg ggcaaaagag caagattcaa tcttcaaaaa agaatttgg    8520 aaaataaaaa taaaagaat acgggatata atagcaatac agttttttac ctccaaggaa    8580
cttatattct agggatagag atagacaata agggctgggt gaggtggctt acgcctgtaa    8640
tcccagcact ttgggaagcc gaggtgggca catcacttga ggtcaggagt tcaagaccag    8700
cctggccgac atggtgaaac cccatctcta ctaaaaatat gaaaattagc tgggtgtggg    8760
ggtgcatgcc tgtaatccca gctacttgga aggctgaggc aggagaatca cttgaacccg    8820
ggagggtgga ggttgccatg agccgagacc atgccactgc actccagcct gggagaccga    8880
gcaaaactcc atctcaaaaa aagaaaaaa aacctcagcc tcccaaagtg ctgggattac    8940
aggcatgagc caccgtgccc gggcttgttt gttttaagag acagggtctc actctgtcac    9000
ccaggctgta ccctattttc tacgtgtctc tgtgtctaag ctcaccaaac ccatccatac    9060
agtgttacct aaaaggactc acgcatgctc cctgtacagt tcccatgaac ttagttcacc    9120
cagcctttgg tgggccaagg tatcgttgag ctctgaagac agatacagct cgggacatgg    9180
ctgagctggc catgactggc agaggagcag ctccaggacc actctgtttt cctagggctt    9240
cctgaccacc cagggcagcc ggaacctgcg ggccgcccat gccttgagc acacatttgc    9300 ccccgtgacc gatggggcca tctccacatt gctgggtctg ctcatgcttg ctggttccca    9360 cttgacttc attgtaaggt agggaggct cgggcaggg aggcagggct caggacaggc    9420
ctgggctgac tccccccaca ccctacccct aggtacttct ttgcggcgct gacagtgctc    9480
acgctcctgg gcctcctcca tggactcgtg ctgctgcctg tgctgctgtc atcctgggc    9540 ccgccgccag aggtgaccac accctcggca ccatccctct actcccagcc caagggacgg    9600
ggtagggaga ggcaagggaa gggacagagc cctgtggccc acagacaggt acctccccaa    9660
caggtgccac cagctgaagg tggcagcctc ctcctttccc cagacaccat gttcctgccc    9720
ctcagccctc ctggcttctt catgggaccc accttagact tttaggatcc agaacaaggt    9780
gcagggtttg ccccaggcct caacatcctg tcgcctgcca gctctcatat cctgctggag    9840
accaacaagg gccccagctt cccaacagtc atggtaatcc ccagcgagat gctaaagggg    9900
acgggagccc caggggcccg tgggcttact ggggctggtg tctccccaca ggtgatacag    9960
atgtacaagg aaagcccaga gatcctgagt ccaccagctc cacagggagg cgggcttagg   10020 tgggggcat cctcctccct gccccagagc tttgccagag tgactacctc catgaccgtg   10080
gccatccacc caccccccct gcctggtgcc tacatccatc cagcccctga tgagcccct   10140 tggtcccctg ctgtcactag ctctggcaac ctcagttcca ggggaccagg tccagccact   10200
```

```
gggtgaaaga gcagctgaag cacagagacc atgtgtgggg cgtgtggggt cactgggaag   10260
cactgggtct ggtgttagac gcaggatgga ccccctggagg gctctgctgc tgctgcatcc   10320
cctctcccga cccagctgtc atgggcctcc ctgatatcca tacagaacag ccaccgattt   10380
gcacatccag gcctgtgtga gcctgtatct gtgtcacttg agagtgaaag ctggcacttg   10440
gggctgcagt gcagccctgt ccccccttccc accccacacc actgcctgcc cagctgacca   10500
agcctgaggg accctccagc acccttccgt ctggtgactc ctgggcaggc tctccatatc   10560
cctgcccacc tcctaccaca tccattattt atatgaaaat gtctatttttt gtagtataca   10620 tacatgttag ctatgatgaa agttttattt tttaaagaat gaaatatatt ctatgtgaag   10680
ctatgatgaa agttttattt tttaaagaat gaaatatatt ctatgtgaac taatctcgaa   10740
agttttattt tttaaagaat gaaatatatt ctatgtgtgc aagtgaacat agcttcagt   10800 tgctttttttt tggacagagt ggggagtttg caagtgaaca ttagctattg gaaggagctt   10860
ctctggtgcc aggacctgag gtattagctt ctctagttct gggtggaaaa gaccccagat   10920
tctggatttt tgtcatatac ttggtaacat catctggatt aagtgcttac tatacaaaac   10980
gataacaaat tttgttggtg tgaaatccta ctgggttcaa tctggagacc gagagcagaa   11040
aaaaaagaac cccactgtgt ggctttcaga gccaccatat tccagcctgc ccgtctctcc   11100
agactcacct ccacctacct gcttcacccg cacgggaaac ggcaaggcag aggggcaaag   11160
ccatgcagca ggtggaaggc gaggtggagg cagatcagga aagcagccag ttgaagcaga   11220
gagaggtcaa cagggtctgg ggagcttctc aggaggtttg tggacccagg gaaaggagcc   11280
aggttccaga gcaacctcca aggcaaaggc ctctgtaagt tggttgtcct gacagccgag   11340 aggtgtctttt ggccagtcag ccagtggatc agttgcggga actgctcaga aactgaggtg   11400
ctagcagtta gtgaggacac agcgtaagtt gtttgttctg tgaaagttga acagctccac   11460
taagcagagg ccttgaagag tggccacagc cctggaatag agcacagagc ctcacctaga   11520
ggcgtgggga ggtttgcaac tgcccccttcc cagccatagc ttaggaccca tagtctagtt   11580
cacatagacc ctgggctcca accacccact caccaggaat gatcccaccc caggaacaat   11640
gcgttctcac atcccacccc acctggacaa aggccaggaa atcatgttct gaccaaaaga   11700
tacaacaaca aaaacaacaa caacaaaaaa cgcctattgc aattgaatcc acgctaaaat   11760
gcctaaaaag ctcaagagaa gcgggtagtt ggcagagaac ctagagtagg gggtgcaacc   11820
agcaggccca agggagggag gctgcatttg ggtccagcag tgtttgggtc accaagaagg   11880
gccttctagg tggagcagag agagctcacc aggccagaat agtgcaaagg gggtcagccc   11940
tcagtgccac ttaccagcgg agtaaccctg ggcaagttag ccagcctcac taagcctccc   12000
catcttcatc tttccaggcc cgaggagatc tagcctctgc ctcccacccc agcaccccct   12060
catcagacac aaggagcgcc actgtctgga caggctgaat tggtcttcgg gtccctaatt   12120
tctcatacgc cattccctct gcctagaaca ctttctcacc tcccccttgat gtgacccccat   12180 atcacccttc gaggtgaatt ggatcggatg ccatctcctc caggaggggt ggggtcgtgc   12240
ctcctgtgag gtcccagtgc ccctgagtgt ctgtgcccgt ctgtttcccc gtccctctct   12300
ctaagcccgg aggcttactg cgggtaagga cggcgggaca ggaccttaac ccctgggacg   12360
aacaccagct ccgcaaagga ctccgcaccc ggcgccgccc acgggtgcg ggtcccagga   12420 ggaccagcag agaggagcat aggagagcaa aggagatcag tgacccatgg cttccccggt   12480
ggcgcggaac agcccggagc cgcctgtgat ttgcataccc atggtgcacc acgaaaagat   12540
accctcaaga tgcttgcact ccctctgtgc gcgcatttct gcactgtttt agagcatgat   12600
```

-continued

```
gcctcttaca cgcatctgtg tgcataaact acatataggg agtgcgtacc acgcaggcat   12660
ccaacaacca taagtgtgtt aagtgttagt tctccctgcg aggttcgaag cggaagtcac   12720
gaatatactc gggtttctct tcaaagcgca taaatctttc gccttttact aaagatttcc   12780
gtggagagaa agttgtgagt ttttattcaa tttttttgagg cctcttattt cctgaggcta   12840
catttttaag tattaaaagt taggcaacta caaaaaaaaa aaaaaa                  12886
```

<210> SEQ ID NO 6
<211> LENGTH: 1447
<212> TYPE: PRT
<213> ORGANISM: Homo sapiens

<400> SEQUENCE: 6

```
Met Ala Ser Ala Gly Asn Ala Ala Glu Pro Gln Asp Arg Gly Gly Gly
1               5                   10                  15

Gly Ser Gly Cys Ile Gly Ala Pro Gly Arg Pro Ala Gly Gly Gly Arg
            20                  25                  30

Arg Arg Arg Thr Gly Gly Leu Arg Arg Ala Ala Ala Pro Asp Arg Asp
        35                  40                  45

Tyr Leu His Arg Pro Ser Tyr Cys Asp Ala Ala Phe Ala Leu Glu Gln
    50                  55                  60

Ile Ser Lys Gly Lys Ala Thr Gly Arg Lys Ala Pro Leu Trp Leu Arg
65                  70                  75                  80

Ala Lys Phe Gln Arg Leu Leu Phe Lys Leu Gly Cys Tyr Ile Gln Lys
                85                  90                  95

Asn Cys Gly Lys Phe Leu Val Val Gly Leu Leu Ile Phe Gly Ala Phe
            100                 105                 110

Ala Val Gly Leu Lys Ala Ala Asn Leu Glu Thr Asn Val Glu Glu Leu
        115                 120                 125

Trp Val Glu Val Gly Gly Arg Val Ser Arg Glu Leu Asn Tyr Thr Arg
    130                 135                 140

Gln Lys Ile Gly Glu Glu Ala Met Phe Asn Pro Gln Leu Met Ile Gln
145                 150                 155                 160

Thr Pro Lys Glu Glu Gly Ala Asn Val Leu Thr Thr Glu Ala Leu Leu
                165                 170                 175

Gln His Leu Asp Ser Ala Leu Gln Ala Ser Arg Val His Val Tyr Met
            180                 185                 190

Tyr Asn Arg Gln Trp Lys Leu Glu His Leu Cys Tyr Lys Ser Gly Glu
        195                 200                 205

Leu Ile Thr Glu Thr Gly Tyr Met Asp Gln Ile Ile Glu Tyr Leu Tyr
    210                 215                 220

Pro Cys Leu Ile Ile Thr Pro Leu Asp Cys Phe Trp Glu Gly Ala Lys
225                 230                 235                 240

Leu Gln Ser Gly Thr Ala Tyr Leu Leu Gly Lys Pro Pro Leu Arg Trp
                245                 250                 255

Thr Asn Phe Asp Pro Leu Glu Phe Leu Glu Glu Leu Lys Lys Ile Asn
            260                 265                 270

Tyr Gln Val Asp Ser Trp Glu Glu Met Leu Asn Lys Ala Glu Val Gly
        275                 280                 285

His Gly Tyr Met Asp Arg Pro Cys Leu Asn Pro Ala Asp Pro Asp Cys
    290                 295                 300

Pro Ala Thr Ala Pro Asn Lys Asn Ser Thr Lys Pro Leu Asp Met Ala
305                 310                 315                 320
```

-continued

```
Leu Val Leu Asn Gly Gly Cys His Gly Leu Ser Arg Lys Tyr Met His
            325                 330                 335

Trp Gln Glu Glu Leu Ile Val Gly Gly Thr Val Lys Asn Ser Thr Gly
                340                 345                 350

Lys Leu Val Ser Ala His Ala Leu Gln Thr Met Phe Gln Leu Met Thr
                355                 360                 365

Pro Lys Gln Met Tyr Glu His Phe Lys Gly Tyr Glu Tyr Val Ser His
            370                 375                 380

Ile Asn Trp Asn Glu Asp Lys Ala Ala Ala Ile Leu Glu Ala Trp Gln
385                 390                 395                 400

Arg Thr Tyr Val Glu Val Val His Gln Ser Val Ala Gln Asn Ser Thr
                    405                 410                 415

Gln Lys Val Leu Ser Phe Thr Thr Thr Leu Asp Asp Ile Leu Lys
                420                 425                 430

Ser Phe Ser Asp Val Ser Val Ile Arg Val Ala Ser Gly Tyr Leu Leu
                435                 440                 445

Met Leu Ala Tyr Ala Cys Leu Thr Met Leu Arg Trp Asp Cys Ser Lys
        450                 455                 460

Ser Gln Gly Ala Val Gly Leu Ala Gly Val Leu Val Ala Leu Ser
465                 470                 475                 480

Val Ala Ala Gly Leu Gly Leu Cys Ser Leu Ile Gly Ile Ser Phe Asn
                    485                 490                 495

Ala Ala Thr Thr Gln Val Leu Pro Phe Leu Ala Leu Gly Val Gly Val
                500                 505                 510

Asp Asp Val Phe Leu Leu Ala His Ala Phe Ser Glu Thr Gly Gln Asn
            515                 520                 525

Lys Arg Ile Pro Phe Glu Asp Arg Thr Gly Glu Cys Leu Lys Arg Thr
            530                 535                 540

Gly Ala Ser Val Ala Leu Thr Ser Ile Ser Asn Val Thr Ala Phe Phe
545                 550                 555                 560

Met Ala Ala Leu Ile Pro Ile Pro Ala Leu Arg Ala Phe Ser Leu Gln
                565                 570                 575

Ala Ala Val Val Val Phe Asn Phe Ala Met Val Leu Leu Ile Phe
                580                 585                 590

Pro Ala Ile Leu Ser Met Asp Leu Tyr Arg Arg Glu Asp Arg Arg Leu
            595                 600                 605

Asp Ile Phe Cys Cys Phe Thr Ser Pro Cys Val Ser Arg Val Ile Gln
    610                 615                 620

Val Glu Pro Gln Ala Tyr Thr Asp Thr His Asp Asn Thr Arg Tyr Ser
625                 630                 635                 640

Pro Pro Pro Pro Tyr Ser Ser His Ser Phe Ala His Glu Thr Gln Ile
                    645                 650                 655

Thr Met Gln Ser Thr Val Gln Leu Arg Thr Glu Tyr Asp Pro His Thr
                660                 665                 670

His Val Tyr Tyr Thr Thr Ala Glu Pro Arg Ser Glu Ile Ser Val Gln
            675                 680                 685

Pro Val Thr Val Thr Gln Asp Thr Leu Ser Cys Gln Ser Pro Glu Ser
            690                 695                 700

Thr Ser Ser Thr Arg Asp Leu Leu Ser Gln Phe Ser Asp Ser Ser Leu
705                 710                 715                 720

His Cys Leu Glu Pro Pro Cys Thr Lys Trp Thr Leu Ser Ser Phe Ala
                725                 730                 735

Glu Lys His Tyr Ala Pro Phe Leu Leu Lys Pro Lys Ala Lys Val Val
```

-continued

```
                740                 745                 750
Val Ile Phe Leu Phe Leu Gly Leu Leu Gly Val Ser Leu Tyr Gly Thr
            755                 760                 765
Thr Arg Val Arg Asp Gly Leu Asp Leu Thr Asp Ile Val Pro Arg Glu
770                 775                 780
Thr Arg Glu Tyr Asp Phe Ile Ala Ala Gln Phe Lys Tyr Phe Ser Phe
785                 790                 795                 800
Tyr Asn Met Tyr Ile Val Thr Gln Lys Ala Asp Tyr Pro Asn Ile Gln
                805                 810                 815
His Leu Leu Tyr Asp Leu His Arg Ser Phe Ser Asn Val Lys Tyr Val
            820                 825                 830
Met Leu Glu Glu Asn Lys Gln Leu Pro Lys Met Trp Leu His Tyr Phe
        835                 840                 845
Arg Asp Trp Leu Gln Gly Leu Gln Asp Ala Phe Asp Ser Asp Trp Glu
    850                 855                 860
Thr Gly Lys Ile Met Pro Asn Asn Tyr Lys Asn Gly Ser Asp Asp Gly
865                 870                 875                 880
Val Leu Ala Tyr Lys Leu Leu Val Gln Thr Gly Ser Arg Asp Lys Pro
                885                 890                 895
Ile Asp Ile Ser Gln Leu Thr Lys Gln Arg Leu Val Asp Ala Asp Gly
            900                 905                 910
Ile Ile Asn Pro Ser Ala Phe Tyr Ile Tyr Leu Thr Ala Trp Val Ser
        915                 920                 925
Asn Asp Pro Val Ala Tyr Ala Ala Ser Gln Ala Asn Ile Arg Pro His
    930                 935                 940
Arg Pro Glu Trp Val His Asp Lys Ala Asp Tyr Met Pro Glu Thr Arg
945                 950                 955                 960
Leu Arg Ile Pro Ala Ala Glu Pro Ile Glu Tyr Ala Gln Phe Pro Phe
                965                 970                 975
Tyr Leu Asn Gly Leu Arg Asp Thr Ser Asp Phe Val Glu Ala Ile Glu
            980                 985                 990
Lys Val Arg Thr Ile Cys Ser Asn  Tyr Thr Ser Leu Gly  Leu Ser Ser
        995                 1000                1005
Tyr Pro  Asn Gly Tyr Pro Phe  Leu Phe Trp Glu Gln  Tyr Ile Gly
    1010                1015                1020
Leu Arg  His Trp Leu Leu Leu  Phe Ile Ser Val Val  Leu Ala Cys
    1025                1030                1035
Thr Phe  Leu Val Cys Ala Val  Phe Leu Leu Asn Pro  Trp Thr Ala
    1040                1045                1050
Gly Ile  Ile Val Met Val Leu  Ala Leu Met Thr Val  Glu Leu Phe
    1055                1060                1065
Gly Met  Met Gly Leu Ile Gly  Ile Lys Leu Ser Ala  Val Pro Val
    1070                1075                1080
Val Ile  Leu Ile Ala Ser Val  Gly Ile Gly Val Glu  Phe Thr Val
    1085                1090                1095
His Val  Ala Leu Ala Phe Leu  Thr Ala Ile Gly Asp  Lys Asn Arg
    1100                1105                1110
Arg Ala  Val Leu Ala Leu Glu  His Met Phe Ala Pro  Val Leu Asp
    1115                1120                1125
Gly Ala  Val Ser Thr Leu Leu  Gly Val Leu Met Leu  Ala Gly Ser
    1130                1135                1140
Glu Phe  Asp Phe Ile Val Arg  Tyr Phe Phe Ala Val  Leu Ala Ile
    1145                1150                1155
```

-continued

```
Leu Thr Ile Leu Gly Val Leu Asn Gly Leu Val Leu Leu Pro Val
    1160            1165                1170
Leu Leu Ser Phe Phe Gly Pro Tyr Pro Glu Val Ser Pro Ala Asn
    1175            1180                1185
Gly Leu Asn Arg Leu Pro Thr Pro Ser Pro Glu Pro Pro Pro Ser
    1190            1195                1200
Val Val Arg Phe Ala Met Pro Pro Gly His Thr His Ser Gly Ser
    1205            1210                1215
Asp Ser Ser Asp Ser Glu Tyr Ser Ser Gln Thr Thr Val Ser Gly
    1220            1225                1230
Leu Ser Glu Glu Leu Arg His Tyr Glu Ala Gln Gln Gly Ala Gly
    1235            1240                1245
Gly Pro Ala His Gln Val Ile Val Glu Ala Thr Glu Asn Pro Val
    1250            1255                1260
Phe Ala His Ser Thr Val Val His Pro Glu Ser Arg His His Pro
    1265            1270                1275
Pro Ser Asn Pro Arg Gln Gln Pro His Leu Asp Ser Gly Ser Leu
    1280            1285                1290
Pro Pro Gly Arg Gln Gly Gln Gln Pro Arg Arg Asp Pro Pro Arg
    1295            1300                1305
Glu Gly Leu Trp Pro Leu Tyr Arg Pro Arg Arg Asp Ala Phe
    1310            1315                1320
Glu Ile Ser Thr Glu Gly His Ser Gly Pro Ser Asn Arg Ala Arg
    1325            1330                1335
Trp Gly Pro Arg Gly Ala Arg Ser His Asn Pro Arg Asn Pro Ala
    1340            1345                1350
Ser Thr Ala Met Gly Ser Ser Val Pro Gly Tyr Cys Gln Pro Ile
    1355            1360                1365
Thr Thr Val Thr Ala Ser Ala Ser Val Thr Val Ala Val His Pro
    1370            1375                1380
Pro Pro Val Pro Gly Pro Gly Arg Asn Pro Arg Gly Gly Leu Cys
    1385            1390                1395
Pro Gly Tyr Pro Glu Thr Asp His Gly Leu Phe Glu Asp Pro His
    1400            1405                1410
Val Pro Phe His Val Arg Cys Glu Arg Arg Asp Ser Lys Val Glu
    1415            1420                1425
Val Ile Glu Leu Gln Asp Val Glu Cys Glu Glu Arg Pro Arg Gly
    1430            1435                1440
Ser Ser Ser Asn
    1445
```

```
<210> SEQ ID NO 7
<211> LENGTH: 54
<212> TYPE: DNA
<213> ORGANISM: Homo sapiens
<220> FEATURE:
<221> NAME/KEY: CDS
<222> LOCATION: (1)..(54)
<223> OTHER INFORMATION:

<400> SEQUENCE: 7 ggg ctt agg tgg ggg gca tcc tcc tcc ctg ccc cag agc ttt gcc aga      48
Gly Leu Arg Trp Gly Ala Ser Ser Ser Leu Pro Gln Ser Phe Ala Arg
1               5                   10                  15 gtg act                                                              54
Val Thr
```

```
<210> SEQ ID NO 8
<211> LENGTH: 18
<212> TYPE: PRT
<213> ORGANISM: Homo sapiens

<400> SEQUENCE: 8

Gly Leu Arg Trp Gly Ala Ser Ser Leu Pro Gln Ser Phe Ala Arg
1               5                   10                  15

Val Thr

<210> SEQ ID NO 9
<211> LENGTH: 54
<212> TYPE: DNA
<213> ORGANISM: Homo sapiens
<220> FEATURE:
<221> NAME/KEY: CDS
<222> LOCATION: (1)..(54)
<223> OTHER INFORMATION:

<400> SEQUENCE: 9 acc tcc atg acc gtg gcc atc cac cca ccc ccc ctg cct ggt gcc tac        48
Thr Ser Met Thr Val Ala Ile His Pro Pro Pro Leu Pro Gly Ala Tyr
1               5                   10                  15 atc cat                                                                 54
Ile His <210> SEQ ID NO 10
<211> LENGTH: 18
<212> TYPE: PRT
<213> ORGANISM: Homo sapiens

<400> SEQUENCE: 10

Thr Ser Met Thr Val Ala Ile His Pro Pro Pro Leu Pro Gly Ala Tyr
1               5                   10                  15

Ile His

<210> SEQ ID NO 11
<211> LENGTH: 54
<212> TYPE: DNA
<213> ORGANISM: Homo sapiens
<220> FEATURE:
<221> NAME/KEY: CDS
<222> LOCATION: (1)..(54)
<223> OTHER INFORMATION:

<400> SEQUENCE: 11 cca gcc cct gat gag ccc cct tgg tcc cct gct gcc act agc tct ggc        48
Pro Ala Pro Asp Glu Pro Pro Trp Ser Pro Ala Ala Thr Ser Ser Gly
1               5                   10                  15 aac ctc                                                                 54
Asn Leu <210> SEQ ID NO 12
<211> LENGTH: 18
<212> TYPE: PRT
<213> ORGANISM: Homo sapiens

<400> SEQUENCE: 12

Pro Ala Pro Asp Glu Pro Pro Trp Ser Pro Ala Ala Thr Ser Ser Gly
1               5                   10                  15

Asn Leu
```

```
<210> SEQ ID NO 13
<211> LENGTH: 33
<212> TYPE: DNA
<213> ORGANISM: Homo sapiens
<220> FEATURE:
<221> NAME/KEY: CDS
<222> LOCATION: (1)..(33)
<223> OTHER INFORMATION:

<400> SEQUENCE: 13 agt tcc agg gga cca ggt cca gcc act ggg tga                          33
Ser Ser Arg Gly Pro Gly Pro Ala Thr Gly
1               5                   10

<210> SEQ ID NO 14
<211> LENGTH: 10
<212> TYPE: PRT
<213> ORGANISM: Homo sapiens

<400> SEQUENCE: 14

Ser Ser Arg Gly Pro Gly Pro Ala Thr Gly
1               5                   10

<210> SEQ ID NO 15
<211> LENGTH: 18
<212> TYPE: DNA
<213> ORGANISM: Homo sapiens
<220> FEATURE:
<221> NAME/KEY: CDS
<222> LOCATION: (1)..(18)
<223> OTHER INFORMATION:

<400> SEQUENCE: 15 agg ccc gag gag atc tag                                              18
Arg Pro Glu Glu Ile
1               5

<210> SEQ ID NO 16
<211> LENGTH: 6
<212> TYPE: PRT
<213> ORGANISM: Homo sapiens

<400> SEQUENCE: 16

Arg Pro Glu Glu Ile Tyr
1               5
```